(12) United States Patent
Giordano et al.

(10) Patent No.: US 9,956,335 B2
(45) Date of Patent: May 1, 2018

(54) MANIFOLD FOR WEARABLE ARTIFICIAL KIDNEY

(71) Applicant: Fresenius Medical Care Holdings, Inc., Waltham, MA (US)

(72) Inventors: Renato Giordano, Newport Beach, CA (US); Phil Swenson, Newport Beach, CA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 392 days.

(21) Appl. No.: 14/650,576

(22) PCT Filed: Dec. 13, 2013

(86) PCT No.: PCT/US2013/074843
§ 371 (c)(1),
(2) Date: Jun. 9, 2015

(87) PCT Pub. No.: WO2014/099631
PCT Pub. Date: Jun. 26, 2014

(65) Prior Publication Data
US 2015/0314056 A1    Nov. 5, 2015

Related U.S. Application Data

(60) Provisional application No. 61/740,974, filed on Dec. 21, 2012.

(51) Int. Cl.
*A61M 1/16* (2006.01)
*A61M 1/34* (2006.01)
*A61M 1/28* (2006.01)

(52) U.S. Cl.
CPC ........ *A61M 1/1633* (2014.02); *A61M 1/1696* (2013.01); *A61M 1/284* (2014.02);
(Continued)

(58) Field of Classification Search
CPC ............. A61M 1/1633; A61M 1/1645; A61M 1/1694; A61M 1/1696; A61M 1/284;
(Continued)

(56) References Cited

U.S. PATENT DOCUMENTS

2007/0060786 A1    3/2007 Gura et al.
2009/0120864 A1    5/2009 Fulkerson et al.
(Continued)

OTHER PUBLICATIONS

International Search Report and Written Opinion of the International Searching Authority issued in corresponding International Patent Application No. PCT/US2013/074843 dated Mar. 25, 2014 (14 pages).

*Primary Examiner* — Andrew Gilbert
*Assistant Examiner* — Courtney Fredrickson
(74) *Attorney, Agent, or Firm* — Kilyk & Bowersox, P.L.L.C.

(57) ABSTRACT

Flexible manifolds configured for use in a wearable artificial kidney are provided and can include an array of manifold plates defining one or more flow path and which are adapted to receive dialysis components including cleaning columns and dialyzers. Wearable artificial kidneys are also provided. For example, a wearable artificial kidney can include a flexible manifold, a first flow path, a second flow path, a third flow path, a first cleaning column, a first dialyzer, a second dialyzer, a second cleaning column, and at least one pump. Systems for performing dialysis are further provided. The systems can include a wearable artificial kidney and manifold inlet and outlet lines for connecting the peritoneum of a dialysis patient to the wearable artificial kidney. Methods for performing dialysis utilizing the flexible manifolds, wearable artificial kidneys, and systems containing the same, are also provided.

20 Claims, 13 Drawing Sheets

(52) U.S. Cl.
CPC ......... *A61M 1/3486* (2014.02); *A61M 1/1621* (2014.02); *A61M 1/1627* (2014.02); *A61M 1/1645* (2014.02); *A61M 1/1694* (2013.01); *A61M 1/287* (2013.01); *A61M 2209/088* (2013.01)

(58) Field of Classification Search
CPC ............ A61M 1/287; A61M 2209/088; A61M 1/1621; A61M 1/1627; A61M 1/28
See application file for complete search history.

(56) References Cited

U.S. PATENT DOCUMENTS

| | | |
|---|---|---|
| 2010/0114012 A1 | 5/2010 | Sandford et al. |
| 2011/0060273 A1 | 3/2011 | Ofsthun et al. |
| 2012/0095402 A1 | 4/2012 | Lande |

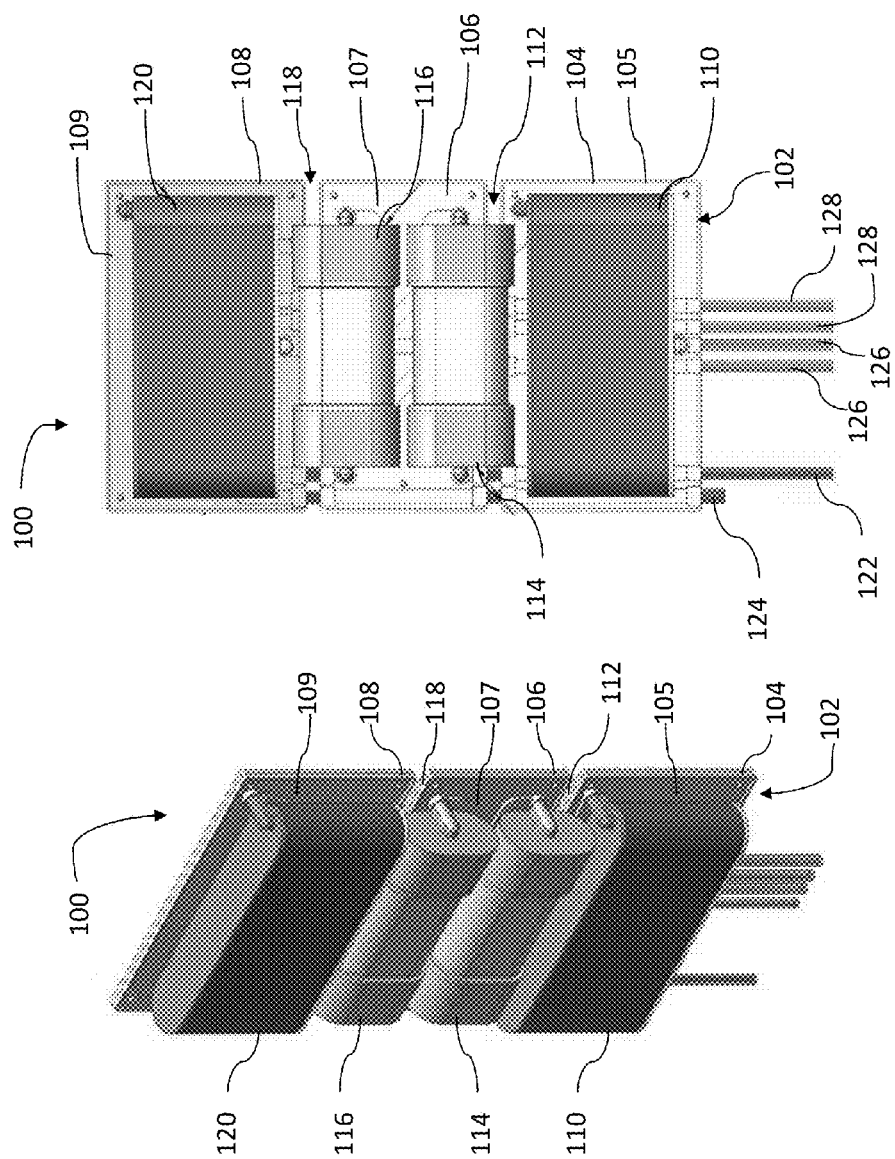

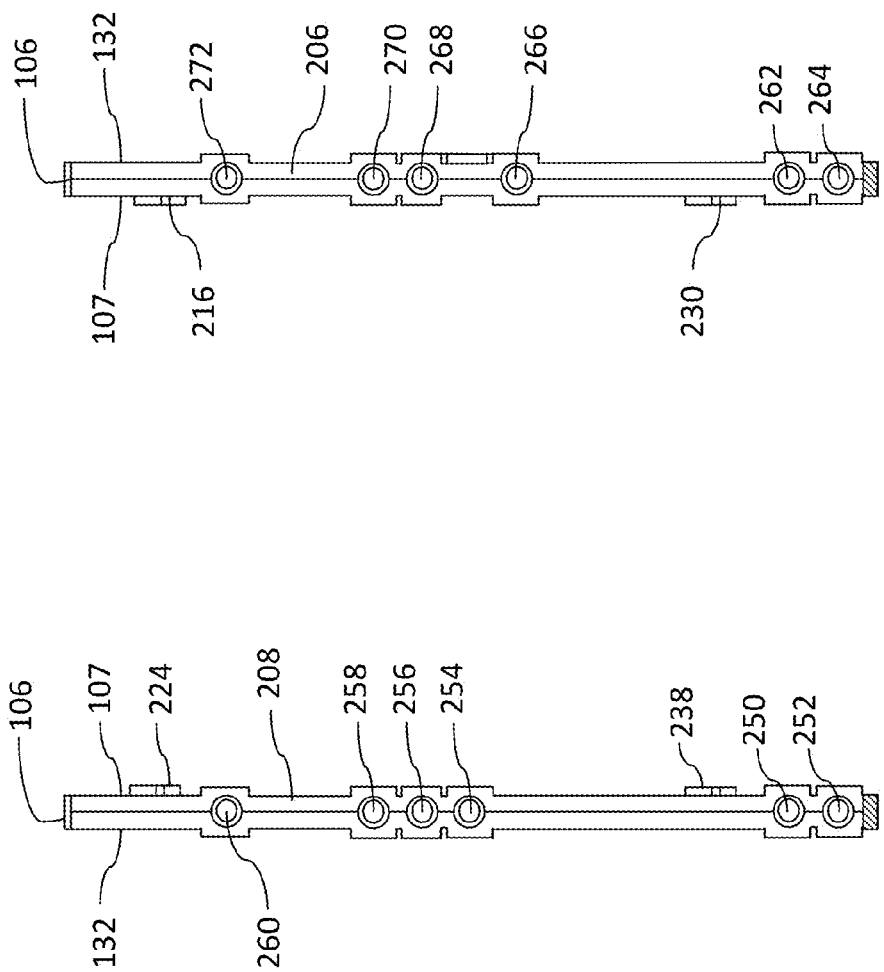

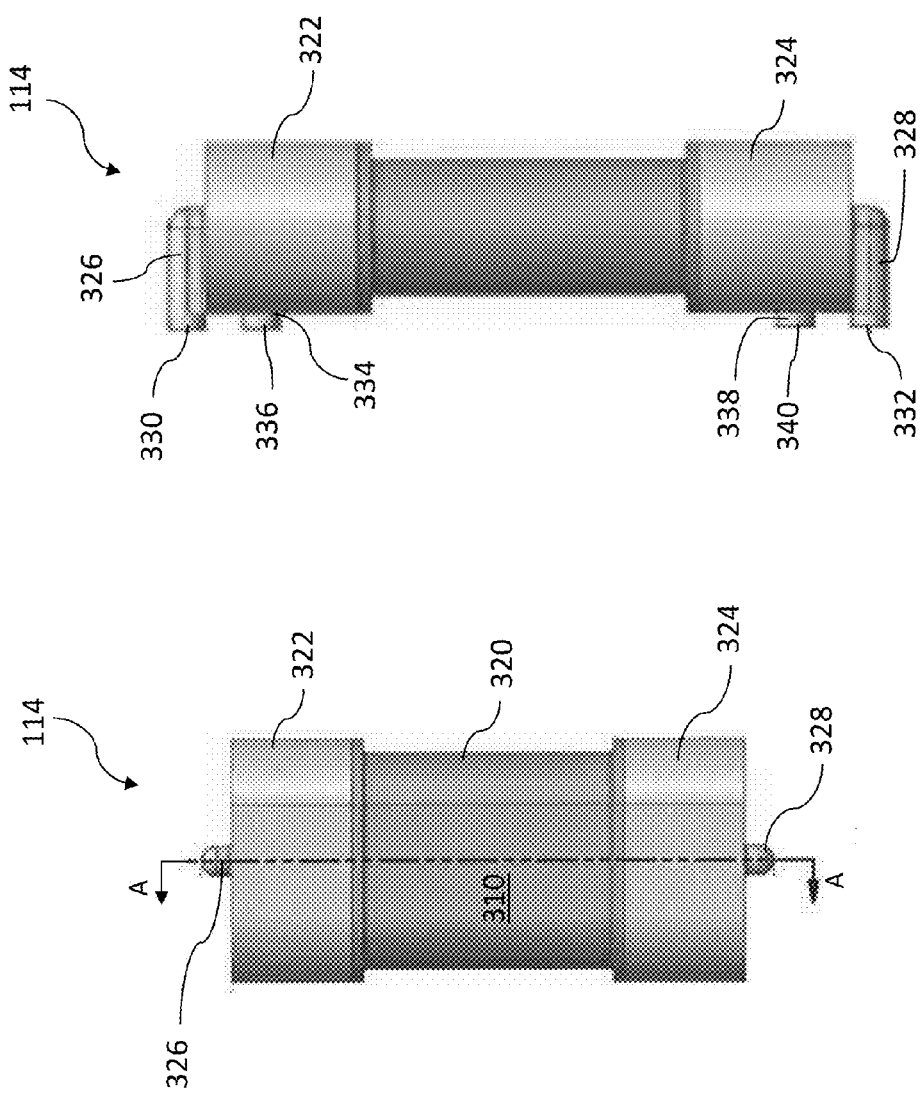

MANIFOLD FOR WEARABLE ARTIFICIAL KIDNEY

This application is a National Stage Application of PCT/US2013/074843, filed Dec. 13, 2013, which claims the benefit under 35 U.S.C. § 119(e) of prior U.S. Provisional Patent Application No. 61/740,974 filed Dec. 21, 2012, which is incorporated in its entirety by reference herein.

FIELD

The present invention relates to sorbent dialysate regeneration, machines, methods, systems, and components thereof.

BACKGROUND

Renal dysfunction or failure and, in particular, end-stage renal disease, causes the body to lose the ability to remove water and minerals and excrete harmful metabolites, maintain acid-base balance, and control electrolyte and mineral concentrations within physiological ranges. Toxic uremic waste metabolites including urea, creatinine, uric acid, and phosphorus accumulate in tissues, which can result in a person's death if the filtration function of the kidney is not replaced.

Dialysis can be used to replace kidney function by removing these waste toxins and excess water. Peritoneal dialysis is a type of dialysis treatment used to replace kidney function in which sterile, dialysis solution (dialysate) is infused into the peritoneal cavity of a patient. The peritoneal membrane serves as a natural dialyzer and toxic uremic waste metabolites and various ions diffuse from the patient bloodstream across the membrane into the dialysis solution. At the same time, water is drawn into the peritoneal cavity by an osmotic gradient. The dialysis solution can be removed, discarded, and replaced with fresh dialysis solution on a semi-continuous or continuous basis. Draining, discarding and replacing the large volumes of solution needed for peritoneal dialysis is inconvenient, unwieldy and expensive, especially for peritoneal dialysis treatment at home.

To address this problem, devices have been designed that reconstitute used dialysate from hemodialysis and/or peritoneal dialysis solution as opposed to discarding it. The dialysate can be regenerated in a machine utilizing a device that eliminates urea from the solution. Typically, the ion exchange resins used in devices such as the REDY® Sorbent System adsorb not only the urea degradation products, but also essential ions such as, for example, calcium and magnesium that have diffused into the dialysate. These ions then generally need to be replaced.

U.S. Patent Application Publication No. US 2011/0060273 A1, which is incorporated by reference in its entirety herein, describes a dialysate regeneration system that can be used at home and moved from one location to another. This system can operate continuously or semi-continuously during periods of dialysis to clear uremic waste metabolites from a patient with renal dysfunction or failure, without overly depleting the patient's body of essential ions, such as, for example, calcium and magnesium. An advantage of this dialysate regeneration system is that it provides patients with the option of a sorbent-based peritoneal dialysis system that can be conveniently used at home. Dialysate cleaning in the dialysate regeneration system enables the use of a much smaller volume of dialysate compared to single pass systems. Even with the portability of such a sorbent-based peritoneal dialysis machine, there exists a need for a machine that can be easily wearable and configured to accept convenient replacement components.

SUMMARY

In accordance with the present invention, a flexible manifold configured for a wearable artificial kidney is provided. The flexible manifold can include an array of manifold plates including a first manifold plate joined to a second manifold plate by a first flexible hinge. The first manifold plate can include a first lateral edge, a first portal, and a first conduit in fluid communication with the first portal. The second manifold plate can include a second lateral edge, a second portal, and a second conduit in fluid communication with the second portal. The first lateral edge can be positioned adjacent to the second lateral edge. The first flexible hinge can include the first manifold plate and the second manifold plate at the first and second lateral edges. The first flexible hinge can include a first flexible tube joining the first conduit and the second conduit to form a first flow path. Additional manifold plates can be added to the array of manifold plates and can be joined to one or more of the other manifold plates using flexible hinges.

In accordance with the present invention, a wearable artificial kidney is provided, for example, a wearable artificial kidney having a flexible manifold, a first flow path, a second flow path, a third flow path, a first cleaning column, a first dialyzer, a second dialyzer, a second cleaning column, and at least one pump. The flexible manifold can include a first manifold plate, a second manifold plate joined to the first manifold plate by a first flexible hinge, and a third manifold plate joined to the second manifold plate by a second flexible hinge. The first flow path can include one or more conduits located in one or more of the first, second, and third manifold plates. The second flow path can include one or more conduits located in one or more of the first, second, and third manifold plates. A third flow path can include one or more conduits located in one or more of the first, second, and third manifold plates. A first cleaning column can be mounted on the first manifold plate and in fluid communication with the second flow path. A first dialyzer can be mounted on the second manifold plate and in fluid communication with the first and second flow paths. A second dialyzer can be mounted on the second manifold plate and in fluid communication with the first and third flow paths. A second cleaning column can be mounted on the third manifold plate in fluid communication with the third flow path. The at least one pump can be configured to cycle a dialysate fluid (dialysate) through the first flow path, a first cleaning fluid through the second flow path, and a second cleaning fluid through the third flow path.

In accordance with the present invention, a system for performing dialysis is provided. The system can include a wearable artificial kidney, a dialysis patient, a manifold inlet line in fluid communication with a peritoneal cavity of the dialysis patient and the first flow path, a manifold outlet line in fluid communication with the peritoneal cavity and the first flow path, a dialysate fluid in the first flow path, a first cleaning fluid in the second flow path, and a second cleaning fluid in the third flow path.

In accordance with the present invention, a method of regenerating dialysate fluid (dialysate) is provided. The method can be performed using any flexible manifold, wearable kidney, system, or a combination thereof, as described herein. The method can include, for example, cycling the dialysate fluid in the first flow path, cycling the first cleaning fluid in the second flow path, and cycling the second cleaning fluid in the third flow path. The method can further include replacing one or more of the first cleaning column, the first dialyzer, the second dialyzer, and the second cleaning column, and repeating the cycling of the dialysate fluid, the first cleaning fluid, and the second cleaning fluid.

BRIEF DESCRIPTION OF THE DRAWINGS

The accompanying drawings, which are incorporated into and constitute a part of the specification, illustrate specific embodiments of the present invention, and taken in conjunction with the detailed description of the specific embodiments, serve to explain the principles of the present invention.

FIG. 1A is a perspective view of a wearable artificial kidney in accordance with the present invention.

FIG. 1B is a plan view of the wearable artificial kidney shown in FIG. 1A.

FIG. 4B is a left, side view of the second manifold plate shown in FIG. 4A.

FIG. 4C is a right, side view of the second manifold plate shown in FIG. 4A.

FIG. 6A is a top, plan view of a dialyzer that can be used as part of a wearable artificial kidney in accordance with the present invention.

FIG. 6B is a side view of the dialyzer shown in FIG. 6A.

DETAILED DESCRIPTION

Figure 1C:
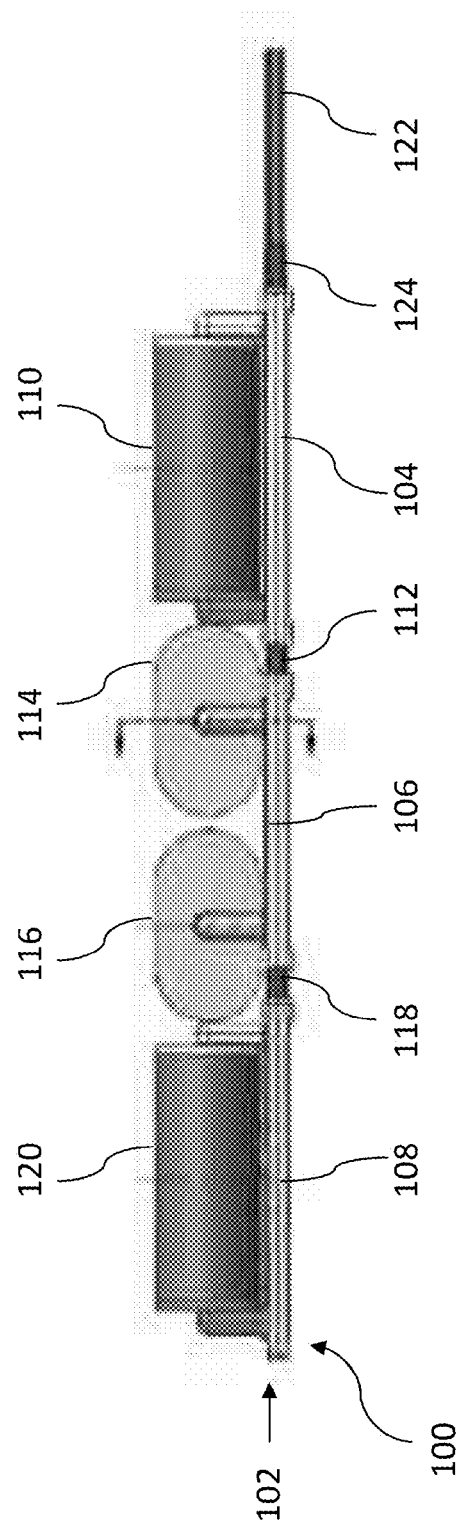
FIG. 1C is a side view of the wearable artificial kidney shown in FIG. 1A.

In accordance with the present invention, a flexible manifold configured for a wearable artificial kidney is provided. The flexible manifold can include an array of manifold plates including a first manifold plate joined to a second manifold plate by a first flexible hinge. The first manifold plate can have a first lateral edge, a first portal, and a first conduit in fluid communication with the first portal. The second manifold plate can have a second lateral edge, a second portal, and a second conduit in fluid communication with the second portal. The first lateral edge can be positioned adjacent to the second lateral edge. The first flexible hinge can join the first manifold plate and the second manifold plate at the first and second lateral edges. The first flexible hinge can include a first flexible tube joining the first conduit and the second conduit to form a first flow path.

The first manifold plate can include a third portal and a third conduit in fluid communication with the third portal. The second manifold plate can include a fourth portal and a fourth conduit in fluid communication with the fourth portal. The first flexible hinge can include a second flexible tube joining the third conduit and the fourth conduit to form a second flow path.

The first manifold plate can include a fifth portal and a fifth conduit in fluid communication with the fifth portal. The second manifold plate can further include a sixth portal and a sixth conduit in fluid communication with the sixth portal. The first flexible hinge can further include a third flexible tube joining the fifth conduit and the sixth conduit to form a third flow path.

The flexible manifold can also include a third manifold plate having a third lateral edge, a seventh portal, and a seventh conduit in fluid communication with the seventh portal. A second flexible hinge can join the second manifold plate and the third manifold plate at the second and third lateral edges. The second flexible hinge can include a fourth flexible tube joining the seventh conduit in fluid communication with the second conduit, the fourth conduit, or the sixth conduit to form a segment of the first, second, or third flow paths.

The first flow path can also include an eighth conduit in the first manifold plate, a ninth conduit in the second manifold plate, a tenth conduit in the second manifold plate, an eleventh conduit in the second manifold plate, a twelfth conduit in the second manifold plate, a thirteenth conduit in the third manifold plate, and the seventh conduit in the third manifold plate. The first flexible hinge can further include a fifth flexible tube joining the eighth conduit and the ninth conduit. The second flexible hinge can further include a sixth flexible tube joining the tenth conduit and the thirteen conduit, a seventh flexible tube joining the thirteenth conduit and the eleventh conduit, and an eighth tube joining the seventh conduit and the twelfth conduit.

The second flow path can also include a fourteenth conduit in the first manifold plate, a fifteenth conduit in the first manifold plate, a sixteenth conduit in the second manifold plate, and a first loop tube forming a fluid communication between the third conduit and the fourteenth conduit. The first flexible hinge further can include a ninth flexible tube joining the fourteenth conduit and the fifteenth conduit in fluid communication.

The third flow path can also include a seventeenth conduit in the first manifold plate, an eighteen conduit in the second manifold plate, a nineteenth conduit in the second manifold plate, a twentieth conduit in the third manifold plate, a twenty-first conduit in the third manifold plate, and a second loop tube forming a fluid communication between the fifth conduit and the seventeenth conduit. The first flexible hinge can include a tenth flexible tube joining the seventeenth conduit and the eighteenth conduit. The second flexible hinge can further include an eleventh flexible tube joining the eighteenth conduit and the twentieth conduit, and a twelfth flexible tube joining the nineteenth conduit and the twenty-first conduit.

The first manifold plate can further include a first cleaning column inlet connector portal in fluid communication with the second flow path and a first cleaning column outlet connector portal in fluid communication with the second flow path. The second manifold plate can further include a first dialyzer dialysate inlet connector portal in fluid communication with the first flow path, a first dialyzer dialysate outlet portal in fluid communication with the first flow path, a first dialyzer cleaning fluid inlet connector portal in fluid communication with the second flow path, and a first dialyzer cleaning fluid outlet connector portal in fluid communication with the second flow path.

The second manifold plate can further include a second dialyzer dialysate inlet connector portal in fluid communication with the first flow path, a second dialyzer dialysate outlet portal in fluid communication with the first flow path, a second dialyzer cleaning fluid inlet connector portal in fluid communication with the third flow path, and a second dialyzer cleaning fluid outlet connector portal in fluid communication with the third flow path. The third manifold plate can further include a second cleaning column inlet connector portal in fluid communication with the third flow path and a second cleaning column outlet connector portal in fluid communication with the third flow path.

The present invention also provides a wearable artificial kidney including a flexible manifold as described herein, a first cleaning column, a first dialyzer, a second dialyzer, and a second cleaning column. The first cleaning column can be in fluid communication with the second flow path and can include a first cleaning column inlet connected to the first cleaning column inlet connector portal and a first cleaning column outlet connected to the first cleaning column outlet connector portal. The first dialyzer can be in fluid communication with the first and second flow paths and can include a first dialyzer inlet connected to the first dialyzer dialysate inlet connector portal, a first dialyzer dialysate outlet connected to the first dialyzer dialysate outlet portal, a first dialyzer cleaning fluid inlet connected to the first dialyzer cleaning fluid inlet connector portal, and a first dialyzer cleaning fluid outlet connector connected to the first dialyzer cleaning fluid outlet connector portal. The second dialyzer can be in fluid communication with the first and third flow paths and can include a second dialyzer inlet connected to the second dialyzer dialysate inlet connector portal, a first dialyzer dialysate outlet connected to the first dialyzer dialysate outlet portal, a second dialyzer cleaning fluid inlet connected to the second dialyzer cleaning fluid inlet connector portal, and a second dialyzer cleaning fluid outlet connector connected to the second dialyzer cleaning fluid outlet connector portal. The second cleaning column can be in fluid communication with the third flow path and can include a second cleaning column inlet connected to the second cleaning column inlet connector portal and a second cleaning column outlet connected to the second cleaning column outlet connector portal.

The wearable artificial kidney can include a flexible manifold, a first flow path, a second flow path, a third flow path, a first cleaning column, a first dialyzer, a second dialyzer, a second cleaning column, and at least one pump. The flexible manifold can include a first manifold plate, a second manifold plate joined to the first manifold plate by a first flexible hinge, and a third manifold plate joined to the second manifold plate by a second flexible hinge. The first flow path can have one or more conduits located in one or more of the first, second, and third manifold plates. The second flow path can have one or more conduits located in one or more of the first, second, and third manifold plates. The third flow path can have one or more conduits located in one or more of the first, second, and third manifold plates. A first cleaning column can be mounted on the first manifold plate and in fluid communication with the second flow path. A first dialyzer can be mounted on the second manifold plate and in fluid communication with the first and second flow paths. A second dialyzer can be mounted on the second manifold plate and in fluid communication with the first and third flow paths. A second cleaning column can be mounted on the third manifold plate in fluid communication with the third flow path. The at least one pump can be configured to cycle a dialysate fluid through the first flow path, a first cleaning fluid through the second flow path, and a second cleaning fluid through the third flow path. One or more of the cleaning columns, dialyzers, pumps, and flexible tubing can be disposable. The pumps can be reusable.

The first dialyzer can include a membrane selectively-permeable to anions. The first cleaning column can have a first layer including activated carbon and a second layer including an anion exchange resin, hydrous zirconium oxide, or a combination thereof. The second dialyzer can include a membrane that is selectively-permeable to urea. The second cleaning column can include a first layer including urease and a second layer including an acid cation exchange resin, an ion exchange sorbent, or a combination thereof.

The first dialyzer can be any suitable type of dialyzer. For example, the first dialyzer can include a membrane selectively-permeable to anions and the first cleaning column can have a first layer including activated carbon and a second layer including an anion exchange resin, hydrous zirconium oxide, or a combination thereof. The second dialyzer can be any suitable type of dialyzer, for example, the second dialyzer can include a membrane selectively-permeable to urea and the second cleaning column can include an acid cation exchange resin, an ion exchange sorbent, or a combination thereof. The second dialyzer can include a membrane selectively-permeable to urea and the second cleaning column can include a first layer having urease and a second layer having an acid cation exchange resin, an ion exchange sorbent, or a combination thereof.

The wearable artificial kidney can also include a first pump in operable communication with the first flow path, a second pump in operable communication with the second flow path, and a third pump in operable communication with the third flow path. The second and third pumps can be peristaltic pumps, the second pump can engage the second loop tube, and the third pump can engage the third loop tube. A single pump can drive one or more rotor, and each rotor can be in operative communication with one or more flow path. The pump can be a diaphragm pump, a peristaltic pump, or any other suitable type of pump. Examples include, but are not limited to: Watson-Marlow 405U/L, Cole-Parmer metering peristaltic pump (HV7420040), Masterflex L/S 16, and the Fresenius Medical Care pump number M30656. The pump can be a micro(small)-gear pump. The one or more pumps can be mounted on, alongside, or remote from the manifold. The pump can be battery powered, for example, with a lithium ion and/or polymer battery pack. The flow rate of the dialysis solution through the dialysate circulation flow path can be from about 50 milliliters per minute (mL/min) to about 300 mL/min, for example, about 100 mL/min.

The wearable artificial kidney can be worn in any suitable or desired manner. The wearable artificial kidney can be worn at or near the abdomen or waist of a dialysis patient. Any suitable attachment device configured to attach the flexible manifold to a dialysis patient can be utilized, for example, a strap, belt, hip-bag, vest, harness, backpack, frame, holster, or a combination thereof. The attachment device can also hold the pumps and/or batteries. The flexible manifold can include a track or other elements that allow it to be connected to or otherwise held by an attachment device. The wearable artificial kidney can have dimensions, including the manifold and attached components, allowing for comfortable wear by a patient. For example, the wearable kidney can have dimensions of about 6.5 inches wide by about 12.5 inches long by about 1.58 inches deep.

A system for performing dialysis is also provided. The system can include a wearable artificial kidney, a dialysis patient, a manifold inlet line in fluid communication with a peritoneal cavity of the dialysis patient and the first flow path, a manifold outlet line in fluid communication with the peritoneal cavity and the first flow path, a dialysate fluid in the first flow path, a first cleaning fluid in the second flow path, and a second cleaning fluid in the third flow path.

A method of regenerating dialysate fluid is also provided. The method can be performed using any flexible manifold, wearable kidney, system, or a combination thereof as described herein. The method can include, for example, cycling the dialysate fluid in the first flow path, cycling the first cleaning fluid in the second flow path, and cycling the second cleaning fluid in the third flow path. The dialysate fluid can be in need of regeneration before entering the flexible manifold and can have been regenerated once the dialysate fluid has exited the flexible manifold. The method can further include replacing one or more of the first cleaning column, the first dialyzer, the second dialyzer, and the second cleaning column, and repeating the cycling of the dialysate fluid, the first cleaning fluid, and the second cleaning fluid.

The wearable artificial kidney and its flexible manifold are described in the context of peritoneal dialysis, but it is to be understood that they can be adapted and configured for use in hemodialysis. The wearable artificial kidney can include a system and/or an apparatus for regenerating dialysate fluid used during peritoneal dialysis and/or hemodialysis. The wearable artificial kidney can be wearable by virtue of having the flexibility to conform to the outside of the human body and to allow for movements relatively unrestricted of the human body while wearing the wearable artificial kidney. The wearable artificial kidney achieves this flexibility by using a manifold that is divided into two or more plates. The two or more plates are joined by a flexible hinge that keeps the plates joined to each other and allows for flexible positioning of the wearable artificial kidney against the outside of the patient, for example, attached to a belt at or near the waist of the patient. The manifold can be divided into three manifold plates including a first manifold plate attached to a second manifold plate by a first flexible hinge, and a third manifold plate connected to the second manifold plate by a second flexible hinge. The flexible hinges can be made of a single member, for example, a belt. The hinge, flexible hinge, or hinges can be made of one or more flexible tubings that, in addition to serving as conduits for dialysate and/or cleaning fluids, also provide a flexible connection and hinge between adjacent manifold plates.

The manifold can be configured to allow insertion of various components into its network of conduits and flow paths. For example, a manifold inlet line can be connected to the manifold to bring spent dialysate into the manifold for processing and regeneration by the wearable artificial kidney. Similarly, a manifold outlet line can be in fluid communication with the manifold allowing regenerated dialysate fluid to exit the manifold and return to the peritoneal cavity of a patient. The manifold can also have one or more dialyzers connected to the various conduits of the manifold. Further, the manifold can have one or more cleaning columns attached to it. In an example, there are a total of two dialyzers and two cleaning columns. The wearable artificial kidney can have a dialysate flow path that flows through one or more conduits that pass through the two dialyzers as well. Each of the two dialyzers can be paired respectively with each of the two cleaning columns. A first cleaning fluid flow path can cycle through a first dialyzer and a first cleaning column. Similarly, a second cleaning fluid flow path can cycle through a second dialyzer and a second cleaning column. It is understood that reference to entry, exit, inlet, outlet, and the like, are made for convenience of discussion, that these are relative terms, and that depending on the direction of fluid flow an entry can become an exit, an inlet can become an outlet, and vice versa.

The operation of the wearable artificial kidney in regenerating spent dialysate can be appreciated by considering, in turn, the three respective flow paths that can be included in the wearable artificial kidney. For example, the dialysate flow path can join the abdomen of a patient through a manifold inlet line that allows for fluid communication between the peritoneal cavity of the patient and the wearable artificial kidney. Dialysate flowing through the manifold inlet line can enter a first plate of the manifold at a manifold entry portal. The dialysate then can flow through a dialysate entry conduit beginning with a first segment of the dialysate entry conduit. The dialysate fluid can flow through a first connector portal, a first flexible hinge, and into a second segment of the dialysate entry conduit after passing through a second connector portal. Dialysate fluid then exits the dialysate entry conduit through an exit portal of the dialysate entry conduit and enters a first dialyzer through a first dialyzer inlet. After passing through the first dialyzer, the dialysate fluid enters an intermediate dialysate conduit through an entry portal of the intermediate dialysate conduit. The dialysate fluid flows through a first segment of the intermediate dialysate conduit, passes through a third connector portal, and leaves the second manifold plate. The dialysate fluid reaches the third manifold plate after passing through a second flexible hinge and through a fourth connector portal into a second segment of the intermediate dialysate conduit. The dialysate fluid passes through a fifth connector portal, through a third flexible hinge, and enters the second manifold plate through a sixth connector portal. The dialysate fluid then flows through a third segment of the intermediate dialysate conduit and exits this conduit through an exit portal of the intermediate dialysate conduit. The dialysate fluid then enters the second dialyzer through an inlet of the second dialyzer. The dialysate fluid, having passed through the dialyzer, exits through an outlet of the second dialyzer, and enters the dialysate exit conduit through an entry portal of the conduit. After passing through a first segment of the dialysate exit conduit, the dialysate fluid leaves the second manifold plate through a seventh connector portal and passes through a fourth flexible hinge to enter the third manifold plate through an eighth connector portal. The dialysate fluid continues to flow through a second segment of the dialysate exit conduit and leaves the third manifold plate through a ninth connector portal. After passing through a fifth flexible hinge, the dialysate fluid enters the second manifold plate through a tenth connector portal and flows through a third segment of the dialysate exit conduit. After passing through an eleventh connector portal and through a sixth flexible hinge, the dialysate fluid passes into the first manifold plate at a twelfth connector portal into a fourth segment of the dialysate exit conduit. Having been regenerated, the dialysate fluid leaves the manifold at a manifold exit portal and flows into a manifold outlet line that returns the regenerated dialysate fluid to the peritoneal cavity of the patient.

The first cleaning fluid flow path forms a cycle that flows through the first dialyzer and the first cleaning column. The first cleaning fluid can exit the first dialyzer and enter the manifold at an entry portal located in the second manifold plate. The entry portal can be an entry to a first cleaning fluid entry conduit. The cleaning fluid passes through a first segment of the first cleaning fluid entry conduit and leaves the second manifold plate through a thirteenth connector portal and flows through a seventh flexible hinge before entering the first manifold plate at a fourteenth connector portal. The first cleaning fluid then flows through a second segment of the first cleaning fluid entry conduit and leaves the first manifold plate at a connector portal before flowing through a first cleaning fluid loop tube. The first cleaning fluid loop tube can be in operable communication with one or more pumps to aid in the movement of the first cleaning fluid through the first cleaning fluid flow path. After flowing through the first cleaning fluid loop tube, the first cleaning fluid reenters the first manifold plate at a connector portal and flows through a third segment of the first cleaning fluid entry conduit. The first cleaning fluid then exits the first cleaning fluid entry conduit through an exit portal. After that, the first cleaning fluid passes through the first cleaning column and exits that column. Having entered the first cleaning column at an inlet, the first cleaning fluid exits through an outlet. The first cleaning fluid returns to the first dialyzer through a first cleaning fluid exit conduit. The first cleaning fluid flows through an entry portal of the first cleaning fluid exit conduit and through a first segment of that conduit. The first cleaning fluid leaves the first manifold plate at a connector portal flowing through an eighth flexible hinge and into the second manifold plate at an eighteenth connector portal. After flowing through a second segment of the first cleaning fluid exit conduit the first cleaning fluid leaves the first cleaning fluid exit conduit through an exit portal. The first cleaning fluid then reenters the first dialyzer, and, after passing through the first dialyzer, begins the first cleaning fluid flow path cycle again.

In a manner analogous to the flow of the first cleaning fluid, the second cleaning fluid flows in a circuit that passes through the second dialyzer and the second cleaning column. The second cleaning fluid exits the second dialyzer and enters a second cleaning fluid entry conduit through an entry portal of the second cleaning fluid entry conduit. The second cleaning fluid exits the second manifold plate at a nineteenth connector portal and, after passing through a ninth flexible hinge, enters the first manifold plate at a twentieth connector portal. The second cleaning fluid passes through a second segment of the second dialysate entry conduit and exits the first manifold plate at a twenty-first connector portal before entering a second cleaning fluid loop tube. The second cleaning fluid loop tube can be in operable communication with one or more pumps to assist the movement of the second cleaning fluid through the second cleaning fluid flow path. The second cleaning fluid reenters the first manifold plate through a twenty-second connector portal and passes through a third segment of the second cleaning fluid entry conduit. The second cleaning fluid exits the first manifold plate at a twenty-third connector portal and passes through a tenth flexible hinge and then enters the second manifold plate at a twenty-fourth connector portal. The second cleaning fluid passes through a fourth segment of the second cleaning fluid entry conduit and exits the second manifold plate at a twenty-fifth connector portal. After flowing through an eleventh flexible hinge, the second cleaning fluid enters the third manifold plate at a twenty-sixth connector portal. The second cleaning fluid passes through a fifth segment of the second cleaning fluid entry conduit and leaves that conduit through an exit portal. The second cleaning fluid then passes through the second cleaning column and exits that column through an outlet. The second cleaning fluid, having left the second cleaning column, passes through an entry portal of a second cleaning fluid exit conduit. The second cleaning fluid exits the third manifold plate through a twenty-seventh connector portal and passes through a twelfth flexible hinge before entering the second manifold plate at a twenty-eighth connector portal. Finally, the second cleaning fluid passes through a second segment of the second cleaning fluid exit conduit, leaves that conduit through an exit portal, and flows into the second dialyzer. The second cleaning fluid, after flowing through the second dialyzer, can begin the cycle of the second cleaning fluid pathway again.

The present invention is useful as a peritoneal dialysis system that removes uremic waste metabolites from a patient suffering from a disorder associated with the accumulation of uremic toxins (for example, chronic kidney failure). The manifold and wearable artificial kidney remove contaminants from spent dialysate. The system can be used to treat a disorder such as, for example, renal disease, including early renal disease, renal dysfunction, or renal failure (for example, end stage renal disease). As used herein, the terms "contaminants," "uremic waste metabolites," and "uremic solutes" include compounds, such as those containing nitrogen, produced by the body as waste products and includes compounds like urea, uric acid, creatinine, β-2-microglobulin, and other materials. See Vanholder et al., Kidney International, 63:1934-1943 (2003), which is incorporated herein by reference in its entirety. Renal failure or dysfunction leads to uremic toxicity, which occurs when the levels of uremic waste metabolites in a patient are elevated compared to the levels of the toxins in individuals with normal renal function.

A patient dialysate outlet and patient dialysate inlet provide outflow from, and inflow to, the peritoneal cavity of the patient. These access ports can include medically appropriate plastic tubing, a double lumen catheter, or two single lumen catheters. Suitable access ports are described, for example, in Cruz et al., Seminars in Dialysis, 14(5): 391-394 (2001), Amerling et al., Seminars in Dialysis, 16(4): 335-340 (2003), and Amerling et al., Seminars in Dialysis, 14(5): 388-390 (2001), which are incorporated herein by reference in their entireties. The peritoneal dialysis system can contain a volume of peritoneal dialysis solution (dialysate) that is infused into and out of the peritoneal cavity of a patient such that the peritoneal dialysis solution removes uremic waste metabolites that diffuse through the peritoneal membrane of the patient into the peritoneal dialysis solution. Any suitable peritoneal dialysis solutions can be used (for example, Delflex®), these solutions being commercially available (for example, from Fresenius Medical Care North America, Waltham, Mass.) and well-known in the art. Commercially available peritoneal dialysis solutions (for example, Delflex®), typically contain calcium (5-7 mg/dL) and magnesium (0.6-1.8 mg/dL). An example of a Delflex® solution formulation is 4.25 g dextrose (glucose), 0.567 g NaCl, 0.392 g sodium lactate, 0.0257 g $CaCl_2$, 0.0152 g $MgCl_2$, and purified water for a total solution volume of 100 ml. A formulation that is substantially free of glucose degradation products can be used. Alternative osmotic agents include sucrose, icodextrin, and trehalose. The volume of dialysate solution can be adjusted to the parameters of a particular patient. For example, a volume of from about 0.2 L to about 5 L, from about 0.5 L to about 3.0 L, or about 2.5 L of peritoneal dialysis solution can be introduced into the peritoneal cavity of the patient.

Components of the wearable artificial kidney can be constructed of any suitable material. For example, the casings (housings) for the dialyzers and cleaning columns can be made from polycarbonate. Hollow fibers for the dialyzers can be of any suitable composition including those available from Fresenius (St. Wendel, Germany), for example, ion rejecting hollow fiber for the first dialyzer and polysulfone and/or PVP hollow fiber for the second dialyzer. An example of a suitable potting material is polyurethane. An example of an ion rejecting hollow fiber is a fiber having cellulose acetate on an interior surface thereof. The membrane area of the semi-permeable hollow fibers can be from about 0.1 $m^2$ to about 5.0 $m^2$, or from about 0.5 $m^2$ to about 2.0 $m^2$, which can depend on the rate of urea transport of the hollow fibers. The interior volumes of the dialyzers with respect to hollow fiber area can be, for example, about 100 cc or from about 80 cc to about 300 cc. The interior volumes of the cleaning columns can be, for example, about 280 cc, or from about 80 cc to about 350 cc. Adjacent layers in the cleaning columns can be separated by either a filter paper layer or a cellulose pad layer.

Any suitable cleaning solution can be used for the first cleaning solution. The first cleaning column can be adapted to remove contaminants from the dialysate including phosphate and organic contaminants, such as, for example, creatinine and β-2-microglobulin. The first cleaning column can include semi-permeable hollow fibers. Appropriate semi-permeable hollow fiber materials include cellulose, nylon, polyvinylidene fluoride, polyvinylpyrrolidone, polysulfone, polyether sulfone, and polypropylene. Hollow fibers with an inner diameter equal to or less than about 210 μm (micrometers), and a wall thickness equal to or less than about 40 μm, made of polysulfone or other suitable material, can be used. The spent dialysate flows through the lumen of the hollow fibers and the contaminants in the dialysate are filtered out of the solution and are transported across the semi-permeable fiber walls. The total membrane area of the polysulfone fibers in the first cleaning column can be, for example, from about 0.1 $m^2$ to about 2.0 $m^2$, from about 0.4 $m^2$ to about 1.0 $m^2$, or about 0.5 $m^2$. The porosity of the hollow fiber walls can be defined in terms of an average pore diameter, above which a molecule will be prevented from passing through the fiber wall and will therefore be retained in the dialysate.

First and second cleaning fluids, as well as peritoneal dialysate, can be added to the wearable artificial kidney by any suitable method. For example, a patient can infuse a bag (1.5 L to 3.0 L) of peritoneal dialysate into the peritoneum via a catheter. A reservoir bag can be used. The wearable artificial kidney can be primed using pumps, gravity-filled from a bag, or using any other suitable equipment or technique. The wearable artificial kidney can be primed in any desired manner. For example, the wearable artificial kidney can be primed with purified water, a dilute salt solution (e.g., 40 meq/L NaCl), 7% sucrose in the cleaning fluid pathway passing through the cleaning column containing zirconium phosphate, or a combination thereof. The solution recirculated through the wearable artificial kidney can be the peritoneal dialysate placed in the peritoneum of the patient. Once primed, the wearable artificial kidney can be attached to a catheter in the patient's abdomen. The dialyzers and cleaning columns can be disposable. Any solutions remaining in the manifold after treatment can be pumped into a drain. The wearable artificial kidney can regenerate the peritoneal dialysate during treatment. Accordingly, dialysate can be replaced after a daily treatment, for example, from about 6 to about 20 hours, or from about 8 hours to about 12 hours. The dialyzers and cleaning column containing hydrous zirconium oxide can be replaced after each treatment. The cleaning column containing zirconium phosphate can be replaced based on patient-dependent parameters. For example, the cleaning column containing zirconium phosphate can last from 4 to 8 hours depending on a patient's weight and uremic status (blood urea concentration).

The first cleaning column can be a microfiltration membrane cartridge, with an average pore diameter for the hollow fibers in a range of from about 0.05 microns to about 2.5 microns. The first cleaning column can be an ultrafiltration membrane cartridge, with an average pore diameter for the hollow fibers in a range of from about 0.003 microns to about 0.1 microns. Examples of microfiltration membrane products include GE Sepa CF PVDF MF JX, a flat sheet membrane, Koch Romicon MF 5.0" cartridge, a hollow fiber membrane, and Pellicon XL Durapore 0.1 micron filter module, and cassettes (GE Osmonics, Minnetonka, Minn.) (Koch Membrane Systems, Inc., Wilmington, Mass.) (Millipore, Inc., Billerica Mass.). Examples of ultrafiltration membrane products include GE Sepa CF Thin Film UF JW, a flat sheet membrane, GE Sepa CF Polysulfone UF EW, a flat sheet membrane, and Amicon PM30 polyethersulfone UF disc, a flat sheet membrane. The first cleaning column can include a hydrous zirconium oxide sorbent cartridge. For example, the cartridge can contain approximately 84 g hydrous zirconium oxide, or from about 70 g to about 100 g, and from about 80 g to about 150 g carbon to fill the remaining space in the cartridge. With flow from the bottom up of the cartridge, a bottom layer of hydrous zirconium oxide can be provided at a depth of from about 2.0 cm to about 3.0 cm, and the top layer of carbon can have a depth of from about 4.0 cm to about 6.0 cm.

The second cleaning column can be adapted to remove urea from the dialysate, while retaining positive ions (cations), including, for example, calcium, magnesium, and sodium ions in the dialysate. Any suitable cleaning fluid can be used in the second cleaning column. The second cleaning column can include semi-permeable hollow fibers adapted for transport of urea across the walls (membrane) of the semi-permeable hollow fibers and adapted to retain at least calcium, magnesium, and sodium ions in the dialysate. The second cleaning column can include a zirconium phosphate sorbent cartridge. For example, the cartridge can contain 220 g zirconium phosphate, from about 60 g to about 90 g of alumina, and from about 10 g to about 50 g of D-10 (jack bean meal on alumina). In the alternative, a cross-linked jack bean meal of about 5 g to about 20 g optionally mixed with carbon can be used in place of the D-10 and alumina.

One approach to cation retention in the dialysate can use hollow fibers that are fabricated from or coated with a cation-rejecting material. For example, a layer can be formed on the inside or outside of the hollow fibers by coating or co-extruding them with a cation-rejecting material. The material forming the selective cation-rejecting layer can be, for example, esterified cellulose or acetylcellulose (cellulose acetate). The selective layer can include acetylcellulose, as described in German Application No. DE 10 2008 003 090.2, filed on Jan. 3, 2008, an English-language translation of which is included in the file history of U.S. Patent Application Publication No. US 2011/0060273 A1, which are incorporated herein by reference in their entireties. A hollow fiber can be produced by a phase inversion process. First, two spinning dope solutions, A and B, are produced. The first spinning dope solution A includes the material for the lumen-side cation-rejecting layer of the hollow fiber membrane, and the second spinning dope solution B includes the material for the support layer. The spinning dope solution for the support layer (the outer layer) can contain 20 wt. % Udel 3500 polysulfone and 5.0 wt. % K90 polyvinylpyrrolidone and also 1.0 wt. % water, in solution in dimethylacetamide, based on the total weight of the solution. The viscosity of this solution can be, for example, about 11,500 mPas. The spinning dope for the lumen-side cation-rejecting layer can include about 30 wt. % cellulose diacetate having a molecular weight of about 29 kDaltons and an acetyl content of about 40 wt. %. (Sigma Aldrich, St. Louis, Mo.). It can be dissolved in dimethylacetamide by stirring. The viscosity of this solution can be about 15,000 mPas.

The two spinning dope solutions can be spun in a suitable volume ratio through a composite hollow fiber die known in the art. In the hollow fiber die, the two solutions are led through mutually concentric die channels which permit the coextrusion of the inner and outer spinning dopes. The two concentric die channels surround an axial channel through which a coagulant for the two spinning dope layers is led. Water can be used as an inner coagulant. The temperature of the die pack (spin pack) can be, for example, about 20° C.

After emerging from the spin pack, the hollow fiber pass through an air gap of about 250 mm before entering a water-filled coagulation bath having a temperature of about 42° C. Subsequently, the composite hollow fiber thus obtained can be rinsed in a rinse bath that is temperature controlled at about 75° C. The output speed of spinning fiber is about 250 mm/s. The hollow fiber thus obtained can be subsequently dried at a temperature of about 95° C. Coagulation and rinse bath volumes and spinning speed can be adjusted so as to obtain a solvent-free regular hollow fiber.

The dry fiber is subsequently reeled. A bundle of the hollow fibers consists of about 2,300 fibers having a total surface area of about 0.4 m². The fiber internal diameter can be about 200 μm. The fiber external diameter can be about 261 μm. The thickness of the cation-rejecting layer can be about 500 nm. The fibers are then molded into a housing and potted with polyurethane to form a module ensuring independent flows along the fiber lumen and along the fiber outside surface. The urea transport rate of cation-rejecting acetylcellulose membranes can be in a range of about 15 g/m²/day (grams per meter square per day) to about 40 g/m²/day.

Alternatively, the cation-rejecting material can be a thin film composite membrane, wherein an interfacial polymerized coating is deposited on the surface of an existing membrane. An interfacial polymerized coating can be deposited by flowing an aqueous solution of a compound containing more than one amine group, such as, for example, p-phenylenediamine, through the inside of a hollow fiber, followed by flowing a non-aqueous solution of an acid chloride containing two or more carbonyl groups and capable of forming a covalent bond with amine, such as, for example, trimesoyl chloride, through the inside of the hollow fiber. From about 0.2% to about 2.0%, or about 2.0%, by weight of p-phenylenediamine dissolved in water, followed by from about 0.5% to about 2.0%, or about 2.0%, by weight of trimesoyl chloride dissolved in hexane, based on the total weight of the total solution, can be used to make a thin film composite membrane on the lumen side of a polysulfone hollow fiber. The membrane can exhibit an ultrafiltration molecular weight cutoff equal to or less than about 50 kDa ($10^3$ Daltons), an internal diameter equal to or less than about 210 μm, and a wall thickness equal to or less than about 40 μm. The urea transport rate of cation rejecting membranes with an interfacial polymerized coating can be in a range of about 20 g/m²/day (grams per meter square per day) to about 60 g/m²/day.

The total volume of the first cleaning solution can be about 1.0 L. The first cleaning solution can be an aqueous solution that can include calcium, magnesium, and sodium in concentrations about equal to the calcium, magnesium, and sodium concentrations in the dialysate, in order to maintain an equilibrium in the concentrations of these cations across the membrane walls of the first cleaning column, and therefore prevent removal of these cations from the dialysate. Alternatively, the first cleaning solution can include calcium, magnesium, and sodium in lower concentrations than the calcium, magnesium, and sodium concentrations in the dialysate, if some removal of these cations from the dialysate is desired.

The pump that pumps the first and/or second cleaning solution can be a peristaltic gear pump, a diaphragm pump, a roller pump, or any other suitable pump. Examples of gear pumps include, but are not limited to: Cole-Parmer (Vernon Hills, Ill.) miniature gear pump EW0701220, Haight Pumps (Evansville, Wis.) 6US Stainless Steel gear pump, Tuthill (Alsip, Ill.) D series gear pump, and Fresenius Medical Care 565342. The pump can be configured to pump the first cleaning solution through the first dialysate cleaning flow path, through the shell side (outside of the hollow fibers) of the cleaning column, and in a direction that is countercurrent to the flow of dialysate through the lumen of the hollow fibers. Pumping can occur at a flow rate that is typically at least equal to the dialysate flow rate, and can be greater than the dialysate flow rate, for example, up to about 800 mL/min.

During operation of the wearable artificial kidney, the first cleaning solution accumulates contaminants such as, for example, creatinine, β-2-microblobulin, and phosphate from the dialysate. The first cleaning flow path can be adapted to remove these contaminants from the first cleaning solution, to maintain a concentration gradient between the dialysate and the first cleaning solution, and therefore continue cleaning the dialysate.

To remove organic contaminants, the first cleaning flow path can include activated carbon, typically charcoal. The activated carbon can have a large surface area per unit volume, a wide range of pore sizes for adsorbing various size uremic toxins, and a high purity and/or USP grade. High purity of the carbon can be achieved through multiple acid and/or water washes to remove any water soluble impurities. The carbon can be in the form of small granules or a coarse powder in order to have less flow restriction (pressure drop) and optimal solute transport. Examples of appropriate activated carbon include: Nuchar® Aquaguard 40 (MeadWestvaco, Glen Allen, Va.), Norit® ROX, and Norit® E Supra (Norit Americas, Marshall, Tex.). Activated carbon can be used that is acid-washed pyrolyzed coal-derived activated carbon, such as that marketed by Calgon Carbon Corporation (Pittsburgh, Pa.).

Phosphorus, as phosphate ($PO_4^{3-}$, $HPO_4^{2-}$, and $H_2PO_4^-$), and sulfate ($SO_4^{2-}$) can be removed by binding to anion exchange resins, or to hydrous zirconium oxide. Appropriate anion exchange resins include DOWEX® 1 (hydroxide form), M-43, 21K XLT, Marathon™ MSA, and M4195 (copper form) (Dow Chemical, Midland, Mich.), and Amberlite™ 96 (Dow Chemical). Hydrous zirconium oxide (for example, zirconium oxide in the acetate or carbonate counter ion form) can be used to bind phosphate and sulfate. The activated carbon powder and hydrous zirconium oxide powder can be in separate compartments in the first cleaning flow path, or the activated carbon powder and hydrous zirconium oxide powder can be layered. The activated carbon powder can be mixed with the hydrous zirconium oxide powder prior to loading the mixture into the first cleaning flow path.

The second cleaning solution can be, for example, an aqueous solution. The total volume of the second cleaning solution can be from about 1.5 L to about 2.0 L. The pump that pumps second cleaning solution can be of the same type as described above for pumping the first cleaning solution. The pump can pump the second cleaning solution through the second dialysate cleaning flow path through the shell side (outside of the semi-permeable hollow fibers) of the second cleaning column in a direction that is countercurrent to the flow of dialysate through the lumen of the hollow fibers, and at a flow rate that can be at least equal to the dialysate flow rate, for example, greater than the dialysate flow rate and up to about 800 mL/min.

During operation of the wearable artificial kidney, the second cleaning solution can accumulate urea from the dialysate. The second fluid flow path can be adapted to remove urea from the second cleaning solution, to maintain a concentration gradient between the dialysate and the second cleaning solution, and therefore to continue cleaning the dialysate.

Urea can be removed by adsorption onto a strong acid cation exchange resin or onto an ion exchange sorbent, or by initially breaking down the urea into ammonia and carbon dioxide gas with a urea-degrading enzyme followed by removal of the ammonia byproduct by adsorption onto the strong acid cation exchange resin or the ion exchange sorbent, and venting of the carbon dioxide to the atmosphere. Any suitable urea-degrading enzyme or catalyst can be used. The urea-degrading enzyme can be naturally occurring (for example, urease from jack beans, other seeds, or bacteria), or produced by recombinant technology (for example, in bacterial, fungal, insect, or mammalian cells that express and/or secrete urea-degrading enzymes), or produced synthetically (for example, synthesized).

The urea-degrading enzyme can be urease. Immobilizing the urease can be advantageous, because immobilization stabilizes the urease while retaining its enzymatic activity, and reduces the likelihood of the urease becoming entrained in the stream of second cleaning solution and producing ammonia downstream of the second cleaning stage, away from the ammonia sorbent. Urease can be immobilized by binding it to aluminum oxide (for example, SORB, HISORB, SORB Technology, Inc., Oklahoma City Okla.), or to a resin, such as, for example, Amberzyme® (Dow Chemical). The enzyme (for example, urease) can also be chemically attached to the membrane or, alternatively, to porous beads or a resin. This attachment both stabilizes the enzyme for extended use and, in the case of attachment to porous beads or resin, allows the urease to be filled and/or replaced in the device. In particular, urease can be chemically attached to the exterior of the polysulfone hollow fiber membrane or to separate fibers or resins. Attachment can be through reactive pendant groups of amino acid portions of the enzyme such as thiol groups, amino groups, or carboxylic acid groups that will not significantly affect the catalytic site. Chemistries that can be used to immobilize enzymes or cross-linked enzyme crystals (CLECs) are well-known in the art (see, for example, Roy et al., Strategies in Making Cross-Linked Enzyme Crystals, Chemical Reviews, 104(9): 3705-3721 (2004), which is incorporated herein by reference in its entirety). In addition, urease can be used in its crystallized form and be mixed with the ion exchange resin or sorbent, for example, for degradation of the urea. Urease enzyme derived from jack bean meal can be immobilized by cross-linking with polyethylenimine, as described in U.S. Patent Application Publication No. US 2010/0078381 A1, which is incorporated herein by reference in its entirety.

The ammonia produced in the enzymatic breakdown of urea can be toxic in concentrations above about 2000 μg/dL (micrograms/deciliter), and also alters the pH away from a physiological acceptable pH, inhibiting the enzymatic activity of urease. Therefore, ammonia can be removed, and can be removed either by adsorption onto polymeric strong acid cation exchange resins, such as, for example, sulfonic acid substituted polystyrene cross-linked with divinyl benzene, or onto an ion exchange sorbent, such as, for example, zirconium phosphate. Any strong acid cation exchange resin with sufficient ammonia (ammonium ion) binding capacity and purity is suitable. Examples of strong acid cation exchange resin include Amberlite™ IRN 77, IRN 97, IRN 99, IR 120, UP 252, CG 15, CG 120, IRC 50, IR 200, and IRA 900 (Dow Chemical), or comparable resins manufactured by Dow Chemical, Mitsubishi, Purolite, Sybron, and Lanxess.

The ammonia can be removed by adsorption onto zirconium phosphate. Zirconium phosphate with improved ammonia binding capacity can prepared as described in U.S. Patent Application Publication No. US 2010/0084330 A1, which is incorporated herein in its entirety by reference. Zirconium phosphate helps control the pH in the vicinity of the urease, maintaining it at or near a physiological acceptable pH, and therefore maintains the enzymatic activity of the urease. The urease and zirconium phosphate can be integrated into at least one cartridge.

Ammonia can be removed by adsorption onto a polymeric strong acid cation exchange resin. The urease and strong acid cation exchange resin can be integrated into at least one cartridge. The second cleaning stage can include an anion exchange resin, to control the pH in the vicinity of the urease, maintaining it at or near a physiological acceptable pH, and therefore maintains the enzymatic activity of the urease. Appropriate anion exchange resins include, for example, DOWEX™ 1 (hydroxide form), M-43, 21 K XLT, Marathon™ MSA, and M4195 (copper form) (Dow Chemical, Midland, Mich.), and Amberlite™ 96 (Dow Chemical).

Polymeric strong acid cation exchange resins or ion exchange sorbents bind ammonia in the form of ammonium ion ($NH_4^+$), and the ability of the resin or sorbent to bind ammonium ion is reduced by competition for binding sites from other positively charged ions (cations), thus requiring larger amounts of ammonia-removing resins or sorbents, and increasing the weight of the cartridge. Therefore, it is desirable to exclude cations from the portion of the cartridge that contains the urease and cation exchange resin or zirconium phosphate sorbent. Cation retention in the dialysate has the additional benefit that the patient's system is not overly depleted of essential ions, such as, for example, calcium ($Ca^{2+}$) and magnesium ($Mg^{2+}$). Therefore, the second cleaning column can include semi-permeable hollow fibers that are fabricated from or coated with a cation-rejecting material that inhibits the transport of cations in either direction across the semi-permeable hollow fibers.

Retaining cations in the dialysate can also generate an osmotic pressure across the hollow fiber wall, due to the concentration of dissolved solutes in the dialysate that are to be balanced on the shell side. Osmotic pressure can be balanced with a substance that is non-toxic, does not react with the urease or ammonia sorbent, has a high enough molecular weight that it does not cross membrane wall into the lumen side of the hollow fiber. Appropriate osmotic agents can include sucrose and other polysaccharides, such as, for example, polydextrin and icodextrin, and raffinose. The osmotic agent can be mixed in with the strong acid cation exchange resins or ion exchange sorbents.

Each cleaning stage can have a volume, for example, of from about 250 mL to about 750 mL, and a weight, for example, of from about 200 g to about 900 g. The peritoneal dialysis system can be used as a dialysate regeneration system for removing contaminants from spent dialysate stored in a tank, that is, while the system is not connected to a patient. The peritoneal dialysis and dialysate regeneration system can include a dialysate circulation flow path including a first cartridge adapted to remove contaminants from spent dialysate. The first cartridge can include a first cleaning solution outlet and a first cleaning solution inlet. A second cartridge can be provided that is adapted to remove urea from the spent dialysate, the second cartridge including semi-permeable hollow fibers adapted for transport of urea across the walls of the semi-permeable hollow fibers and adapted to retain at least calcium, magnesium, and sodium ions in the spent dialysate. The second cartridge can include a second cleaning solution outlet and a second cleaning solution inlet. A peritoneal dialysis cycler can be provided and configured to transfer a predetermined quantity of dialysate into a peritoneal cavity of a patient, direct spent dialysate from the peritoneal cavity of the patient into the first cartridge and the second cartridge, and introduce regenerated dialysate into the peritoneal cavity of the patient. A suitable cycler is described in U.S. Patent Application Publication No. US 2008/0058712 A1 and in U.S. Pat. No. 7,935,074 B2, which are incorporated by reference herein in their entireties, and available as the Liberty® cycler from Fresenius Medical Care North America.

A dialysis cycle can include infusing a volume of dialysate into the peritoneal cavity of a patient, waiting for a dwell time of about 2 hours, draining a volume of dialysate approximately equal to the volume of fluid (ultrafiltrate) accumulated in the peritoneal cavity of the patient during the dwell time (typically about 0.8 liters), circulating the dialysate through the portable peritoneal dialysis dialysate regeneration system continuously for about 8 hours, draining the entire volume of dialysate. The cycle can then include infusing another volume of dialysate into the patient's peritoneal cavity, waiting for a dwell time of about 2 hours, and then draining the dialysate out of the patient's peritoneal cavity, leaving the cavity relatively dry for about 12 hours before beginning another peritoneal dialysis cycle. The peritoneal dialysis system can circulate dialysate for a portion of the peritoneal dialysis cycle, but the cycle can also include periods when the dialysate is not being circulated. This type of cycle can be referred to herein as a semi-continuous operation of the peritoneal dialysis system. The system can include a bypass flow path that bypasses a patient while cleaning the dialysate. The system can include bypass flow paths around the first and second cartridges, to clean the dialysate using only one of the first or second cartridges.

With reference to the Drawings, FIG. 1A is a perspective view of a wearable artificial kidney 100. Wearable artificial kidney 100 includes a manifold 102. Manifold 102 includes a first manifold plate 104 that has a first manifold plate top surface 105, a second manifold plate 106 that has a second manifold plate top surface 107, and a third manifold plate 108 having a third manifold plate top surface 109. A first cleaning column 110 is connected to first manifold plate 104. First manifold plate 104 is connected to second manifold plate 106 via a first flexible hinge 112. A first dialyzer 114 and a second dialyzer 116 are connected to second manifold plate 106. A second flexible hinge 118 connects second manifold plate 106 to third manifold plate 108. A second cleaning column 120 is connected to third manifold plate 108.

FIG. 1B is a plan view of wearable artificial kidney 100 shown in FIG. 1A. In addition to the elements shown and described for wearable artificial kidney 100 in FIG. 1A, FIG. 1B also shows manifold inlet line 122 in fluid communication with manifold 102 and manifold outlet line 124 similarly in fluid communication with manifold 102. Also visible in part, in FIG. 1B, are first cleaning fluid loop lines 126 and second cleaning fluid loop lines 128.

FIG. 1C is a side view of wearable artificial kidney 100 shown in FIG. 1A. Again, first cleaning column 110 is shown connected to first manifold plate 104, first dialyzer 114 and second dialyzer 116 are shown connected to second manifold plate 106, and second cleaning column 120 is shown attached to third manifold plate 108. Manifold inlet line 122 and manifold outlet line 124 are in fluid communication with manifold 102. First flexible hinge 112 and second flexible hinge 118 connect the manifold plates together.

Figure 1D:
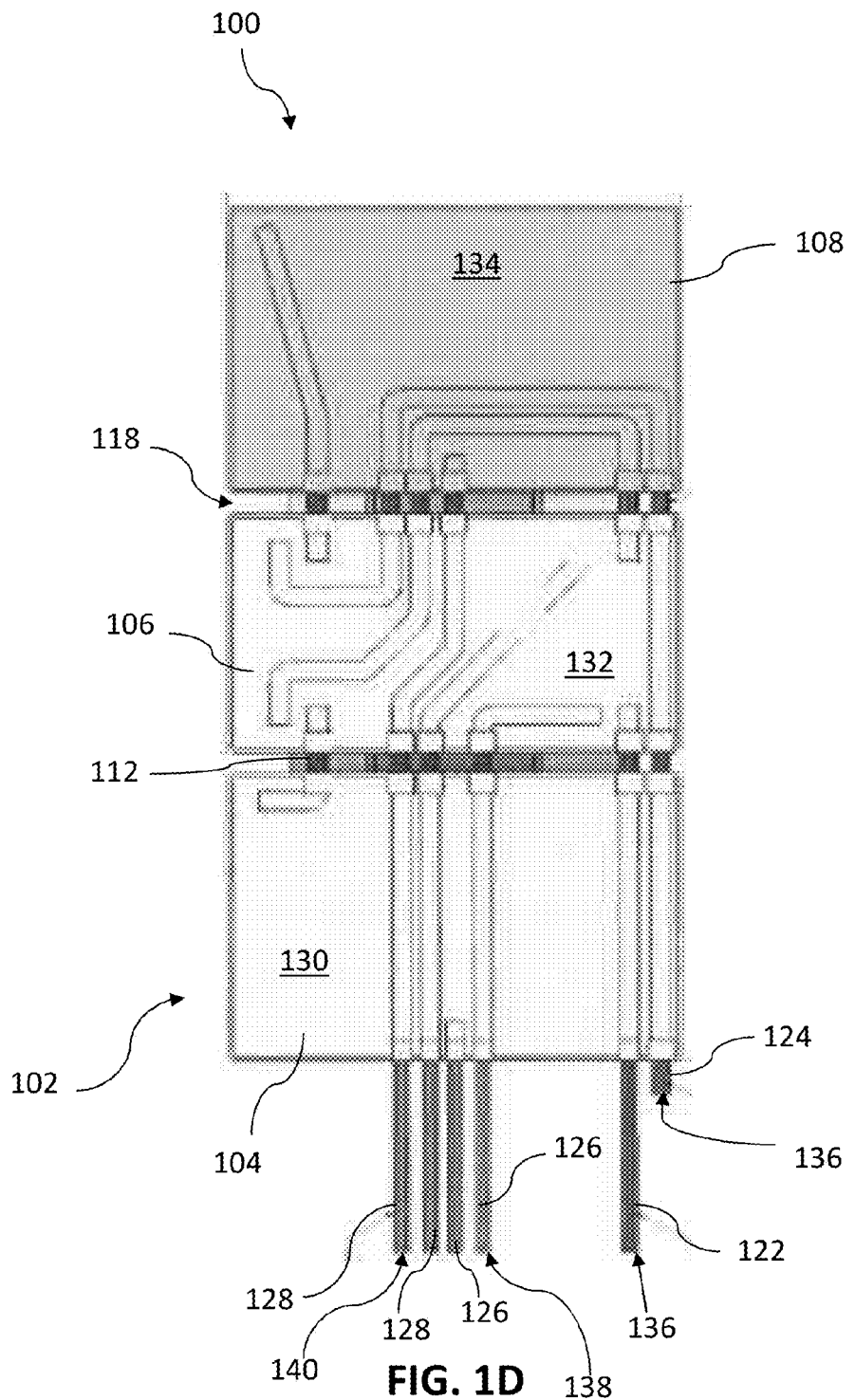
FIG. 1D is a rear plan view of the wearable artificial kidney shown in FIG. 1A.

FIG. 1D is a rear, plan view of wearable artificial kidney 100 shown in FIG. 1A. Manifold 102 is again visible with the rear surfaces of the three manifold plates visible as first manifold plate back surface 130, second manifold plate back surface 132, and third manifold plate back surface 134. First manifold plate 104 is connected to second manifold plate 106 via first flexible hinge 112, and similarly, second manifold plate 106 is connected to third manifold plate 108 via second flexible hinge 118. Dialysate flow path 136 is shown as including manifold inlet line 122 and manifold outlet line 124. First cleaning fluid flow path 138 is shown including first cleaning fluid loop lines 126 and second cleaning fluid flow path 140 is shown including second cleaning fluid loop lines 128.

Figure 2:
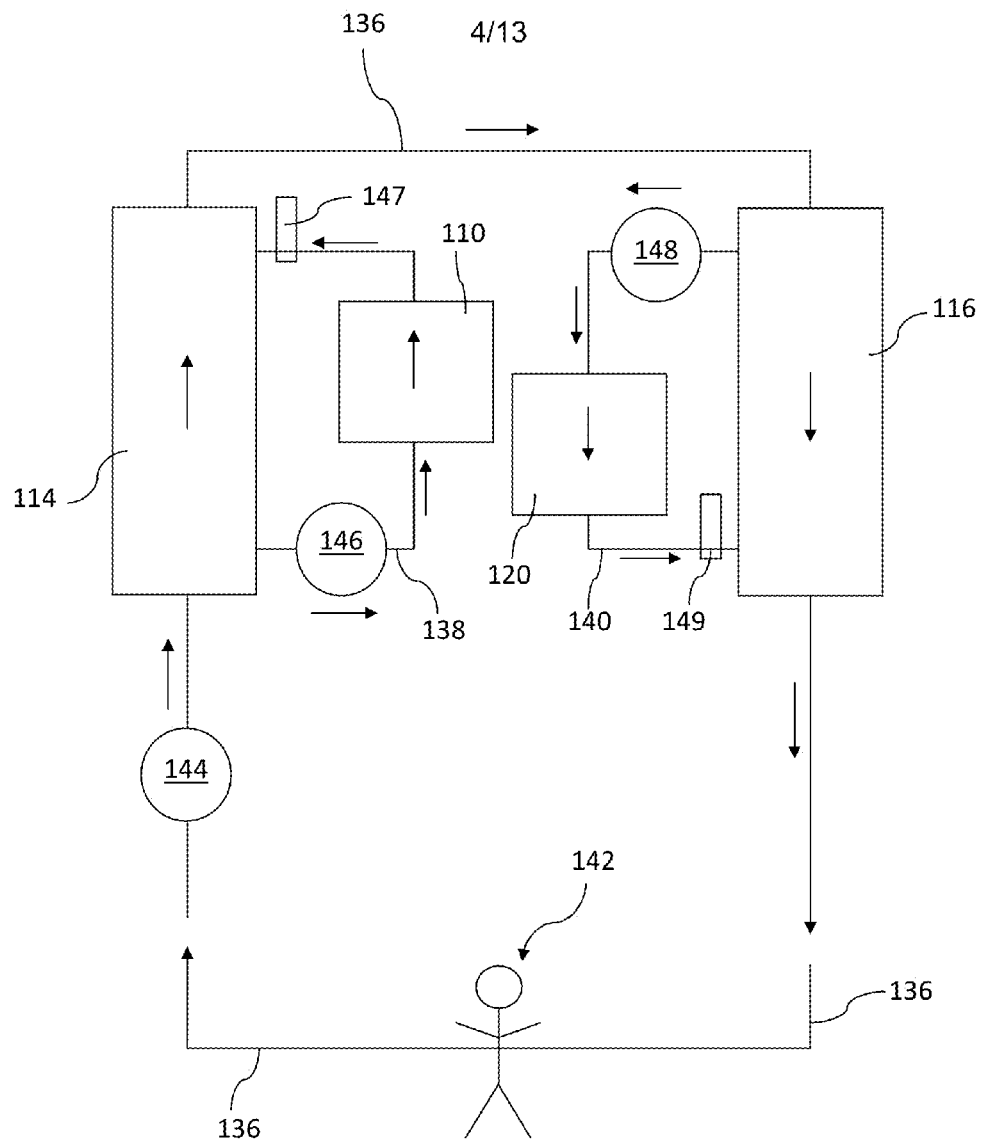
FIG. 2 is a schematic diagram showing flow paths for a wearable artificial kidney in accordance with the present invention.

FIG. 2 is a schematic diagram of dialysate flow path 136, first cleaning fluid flow path 138, and second cleaning fluid flow path 140, with respect to wearable artificial kidney 100. Dialysate fluid leaves a patient 142 and is pumped through the dialysate flow path 136 using a dialysate flow path pump 144. The dialysate fluid passes through first dialyzer 114, and then through second dialyzer 116, before returning to patient 142. The first cleaning fluid cycles through first cleaning fluid flow path 138 from first dialyzer 114, is pumped by first cleaning fluid flow path pump 146 so it passes through first cleaning column 110, and then passes through a first cleaning fluid vent 147, before returning to first dialyzer 114. The second cleaning fluid flows from second dialyzer 116 along second cleaning fluid flow path 140. The second cleaning fluid is pumped by second cleaning fluid flow path pump 148 and passes through second cleaning column 120, and through second cleaning fluid vent 149, before returning to second dialyzer 116.

Figure 3A:
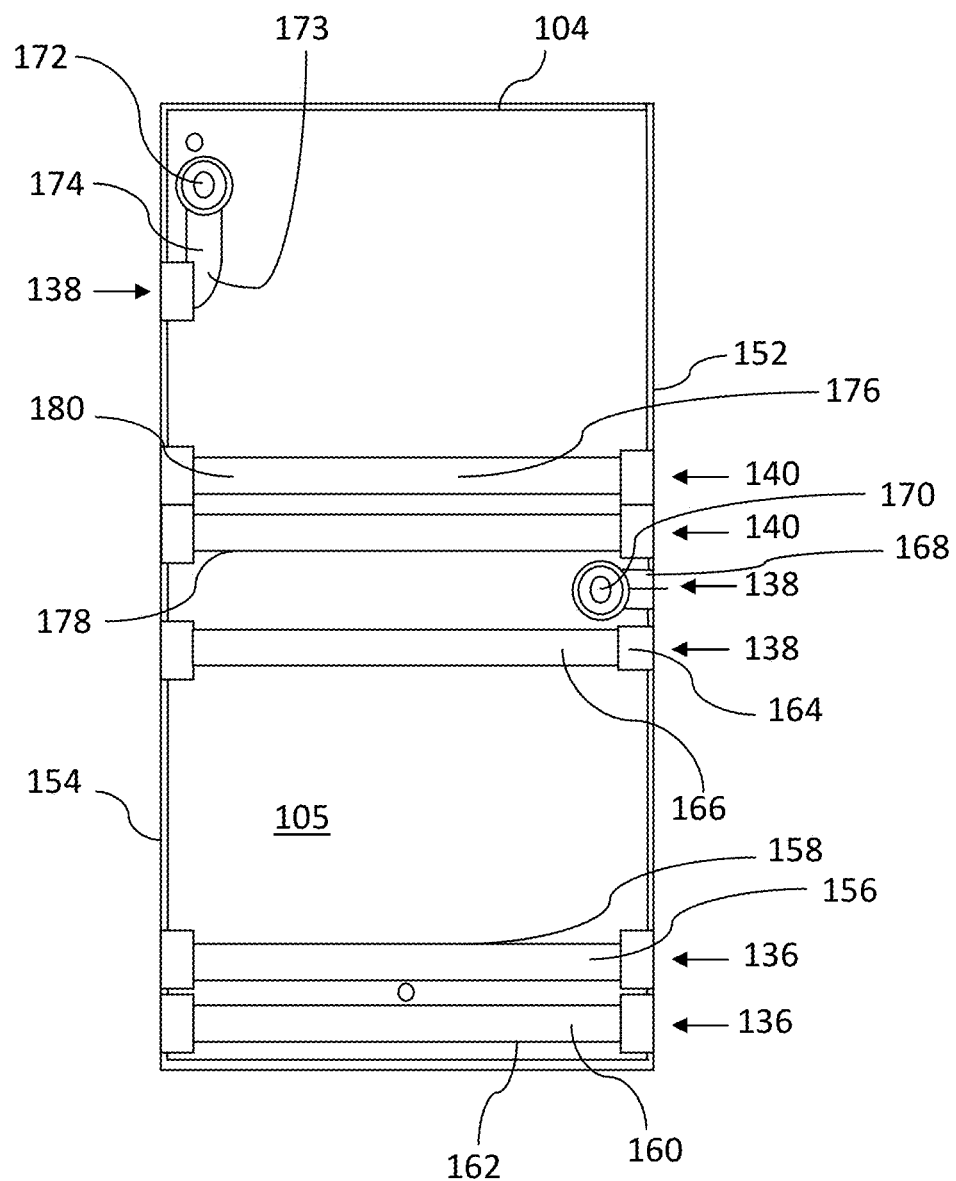
FIG. 3A is a top, plan view of a first manifold plate that can form part of a wearable artificial kidney in accordance with the present invention.

FIG. 3A is a plan view of first manifold plate 104 showing first manifold plate top surface 105, as well as various conduit and flow path elements of wearable artificial kidney 100. First manifold plate 104 includes a first manifold plate first lateral edge 152 and a first manifold plate second lateral edge 154 which are parallel to one another. A dialysate entry conduit 156 includes a first dialysate flow path segment 158, which extends between first manifold plate first lateral edge 152 and first manifold plate second lateral edge 154. Dialysate exit conduit 160 includes a fourth segment of the dialysate exit conduit 162, that extends between first manifold plate second lateral edge 154 and first manifold plate first lateral edge 152. First cleaning fluid entry conduit 164 includes a second segment 166 of first cleaning fluid entry conduit 164 that extends between first manifold plate first lateral edge 152 and first manifold plate second lateral edge 154. First cleaning fluid entry conduit 164 also includes a third segment 168 that extends from first manifold plate first lateral edge 152 to an exit portal 170 of first cleaning fluid entry conduit 164. First cleaning fluid exit conduit 173 includes a first segment 174 of first cleaning fluid exit conduit 173 that extends from first manifold plate second lateral edge 154 to entry portal 172 of first cleaning fluid exit conduit 173. Second cleaning fluid entry conduit 176 includes a second segment 178 and a third segment 180, both of which extend between first manifold plate first lateral edge 152 and first manifold plate second lateral edge 154.

Figure 3C:
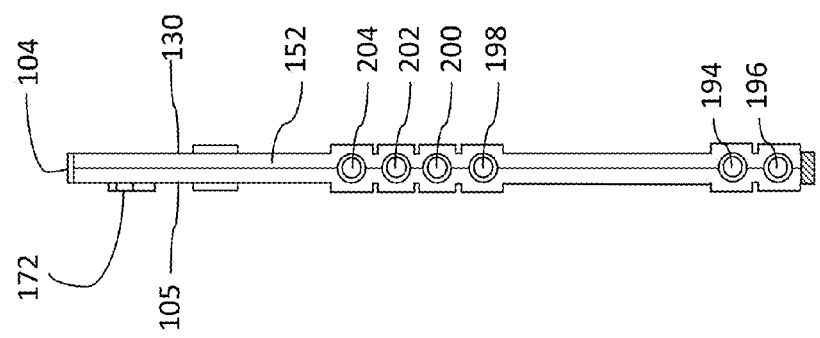
FIG. 3C is a right, side view of the first manifold plate shown in FIG. 3A.
Figure 3B:
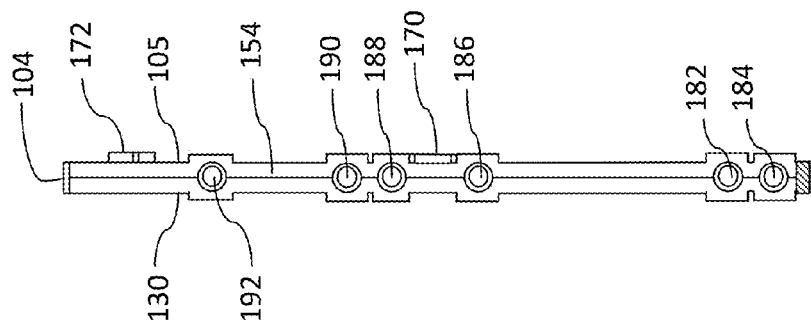
FIG. 3B is a left, side view of the first manifold plate shown in FIG. 3A.

FIG. 3B is a left, side view of first manifold plate 104 showing first manifold plate second lateral edge 154. Exit portal 170 of first cleaning fluid entry conduit 164 and entry portal 172 of first cleaning fluid exit conduit 173 are visible. A series of connector portals are shown along first manifold plate second lateral edge 154, between first manifold plate top surface 105 and first manifold plate back surface 130. These include first connector portal 182, twelfth connector portal 184, fourteenth connector portal 186, twentieth connector portal 188, twenty-third connector portal 190, and seventeenth connector portal 192.

FIG. 3C is a right, side view of first manifold plate 104, shown in FIG. 3A. FIG. 3C shows first manifold plate first lateral edge 152 between first manifold plate top surface 105 and first manifold plate back surface 130. Entry portal 172 of first cleaning fluid exit conduit 173 is visible in this view. A series of connector portals are arrayed along first manifold plate first lateral edge 152. These connector portals include entry portal 194 of dialysate entry conduit 156, exit portal 196 of dialysate exit conduit 160, fifteenth connector portal 198, sixteenth connector portal 200, twenty-first connector portal 202, and twenty-second connector portal 204.

Figure 4A:
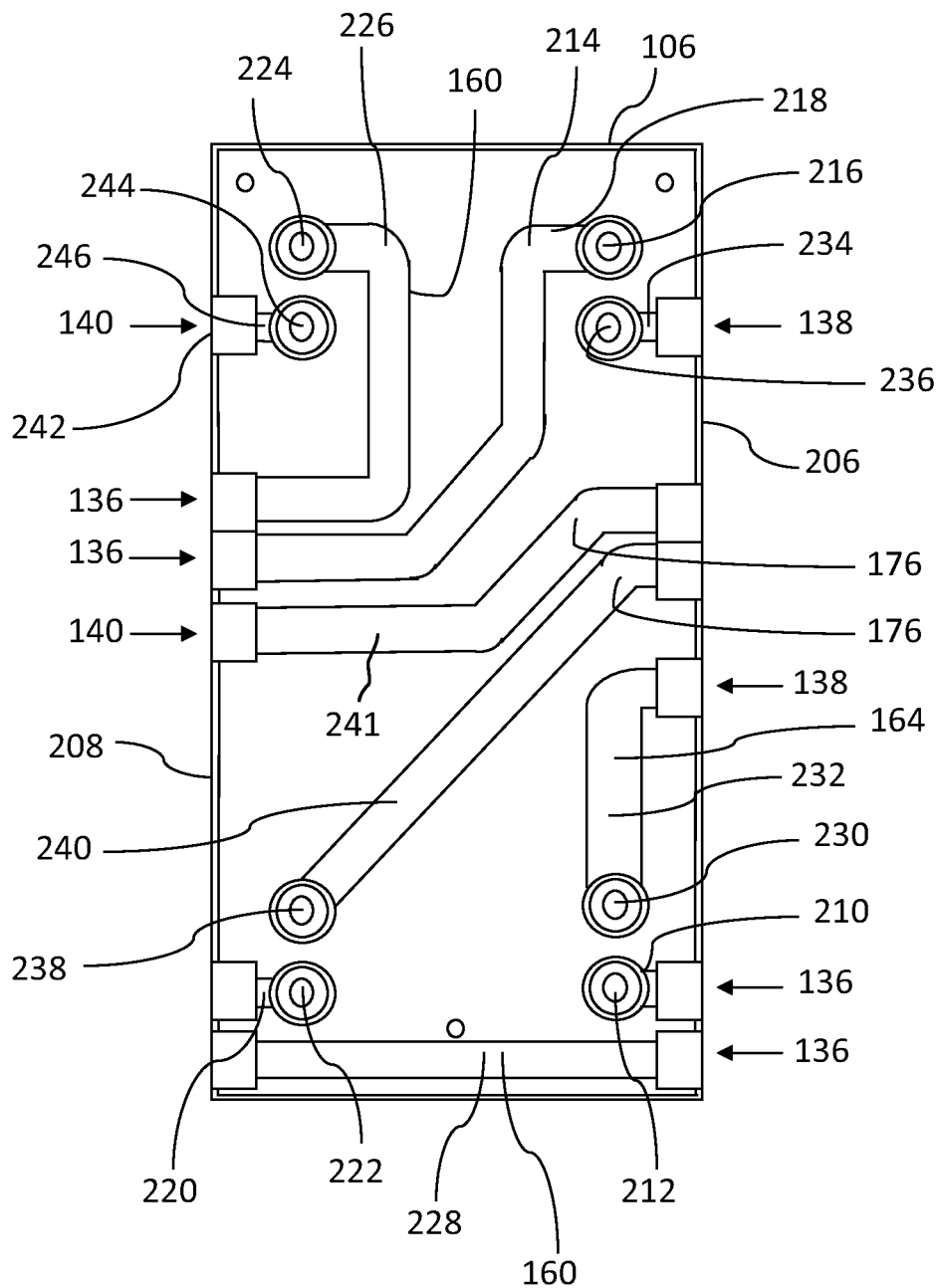
FIG. 4A is a top, plan view of a second manifold plate that can form part of a wearable artificial kidney in accordance with the present invention.

FIG. 4A is a top, plan view of second manifold plate 106. Running along parallel sides of second manifold plate 106 are a second manifold plate first lateral edge 206 and a second manifold plate second lateral edge 208. A second segment 210 of dialysate entry conduit 156 is in fluid communication with exit portal 212 of dialysate entry conduit 156. Intermediate dialysate conduit 214 includes an entry portal 216 in fluid communication with a first segment 218 of intermediate dialysate conduit 214 and a third segment 220 of the intermediate dialysate conduit 214 extends from second manifold plate second lateral edge 208 to an exit portal 222 of intermediate dialysate conduit 214. An entry portal 224 of dialysate exit conduit 160 is in fluid communication with a first segment 226 of dialysate exit conduit 160. A third segment 228 of dialysate exit conduit 160 extends between second manifold plate second lateral edge 208 and second manifold plate first lateral edge 206. Entry portal 230 of the first cleaning fluid entry conduit 164 is in fluid communication with first segment 232 of that conduit. Second segment 234 of first cleaning fluid exit conduit 173 (FIG. 3A) is in fluid communication with exit portal 236 of that conduit. Entry portal 238 of second cleaning fluid entry conduit 176 is in fluid communication with first segment 240 of second cleaning fluid entry conduit 176. Second cleaning fluid entry conduit 176 also includes a fourth segment 241. Second cleaning fluid exit conduit 242 includes an exit portal 244 and a second segment 246 of second cleaning fluid exit conduit 242.

FIG. 4B is a left, side view of second manifold plate 106 shown in FIG. 4A. Second manifold plate second lateral edge 208 lies between second manifold plate top surface 107 and second manifold plate back surface 132. Entry portal 224 and entry portal 238 are visible in this view. An array of connector portals is located along second manifold plate second lateral edge 208. These connector portals include sixth connector portal 250, tenth connector portal 252, twenty-fifth connector portal 254, third connector portal 256, seventh connector portal 258, and twenty-eighth connector portal 260.

FIG. 4C is a right, side view of second manifold plate 106 shown in FIG. 4A. Second manifold plate first lateral edge 206 lies between second manifold plate top surface 107, and second manifold plate back surface 132. Entry portal 216 and entry portal 230 are visible in this view. An array of connector portals is located along second manifold plate first lateral edge 206. These connector portals include second connector portal 262, eleventh connector portal 264, thirteenth connector portal 266, nineteenth connector portal 268, twenty-fourth connector portal 270, and eighteenth connector portal 272.

Figure 5B:
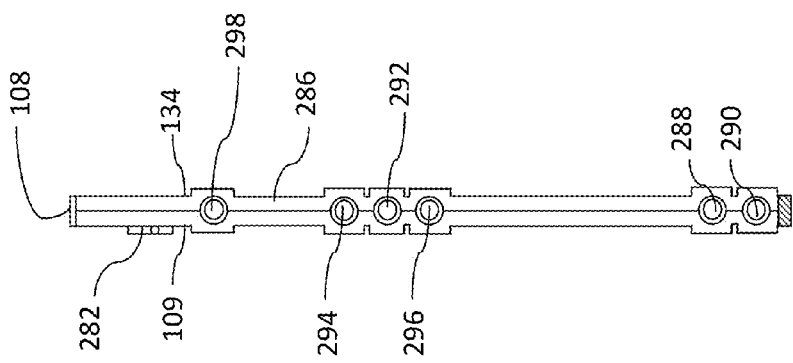
FIG. 5B is a right, side view of the third manifold plate shown in FIG. 5A.
Figure 5A:
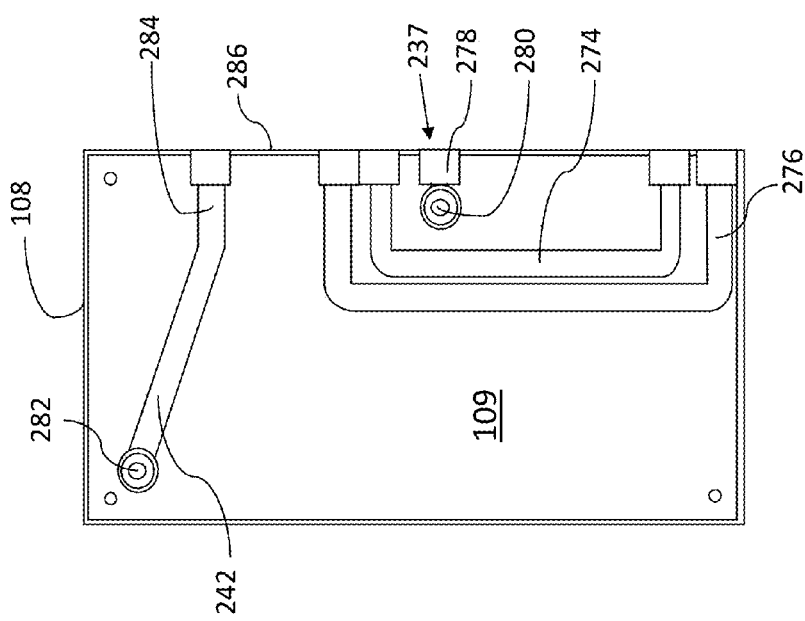
FIG. 5A is a top, plan view of a third manifold plate that can be used as part of a wearable artificial kidney in accordance with the present invention.

FIG. 5A is a top, plan view of third manifold plate 108. Second segment 274 of intermediate dialysate conduit 214 extends from one portion of lateral edge 286 of third manifold plate 108 to another portion of that same lateral edge. Second segment 276 of dialysate exit conduit 160 extends from a portion of lateral edge 286 to another portion of that same lateral edge. A fifth segment 278 of second cleaning fluid entry conduit 237 extends from lateral edge 286 to exit portal 280 of second cleaning fluid entry conduit 237. Entry portal 282 of second cleaning fluid exit conduit 242 extends from third manifold plate top surface 109 and is in fluid communication with first segment 284 of second cleaning fluid exit conduit 242 that extends to lateral edge 286.

FIG. 5B is a right, side view of third manifold plate 108, shown in FIG. 5A. Lateral edge 286 lies between third manifold plate top surface 109 and third manifold plate back surface 134. An array of connector portals lies along lateral edge 286. These connector portals include fifth connector portal 288, ninth connector portal 290, fourth connector portal 292, eighth connector portal 294, twenty-sixth connector portal 296, and twenty-seventh connector portal 298.

FIG. 6A is a top, plan view of first dialyzer 114, the description of which also applies to second dialyzer 116. First dialyzer 114 includes a dialyzer exterior surface 310. First dialyzer 114 includes a dialyzer main-housing 320 and on either end of the same, a dialyzer first end cap 322 and a dialyzer second end cap 324. A dialyzer dialysate inlet 326 is connected to dialyzer first end cap 322 and a dialyzer dialysate outlet 328 is connected to dialyzer second end cap 324.

FIG. 6B is a side view of first dialyzer 114 shown in FIG. 6A. Dialyzer inlet 326 includes a dialyzer dialysate entry portal 330. Dialyzer dialysate outlet 328 includes a dialyzer dialysate exit portal 332. Dialyzer first end cap 322 further includes a dialyzer cleaning fluid outlet 334 that has a dialyzer cleaning fluid exit portal 336. Dialyzer second end cap 324 further includes a dialyzer cleaning fluid inlet 338 and a dialyzer cleaning fluid entry portal 340.

Figure 6C:
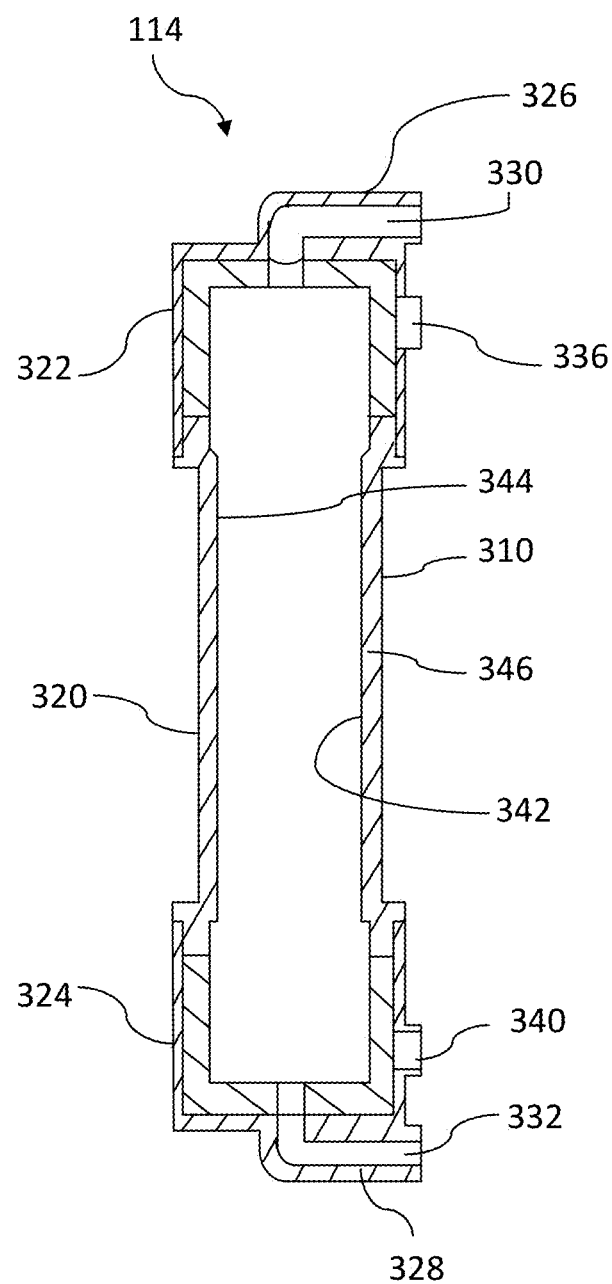
FIG. 6C is a cross-sectional view of the dialyzer shown in FIG. 6A, taken along line A-A in FIG. 6A.

FIG. 6C is a cross-sectional view of first dialyzer 114 shown in FIG. 6A. Dialyzer main housing 320 is again shown with dialyzer first end cap 322, connected on one end, and dialyzer second end cap 324, connected on the opposite end. Dialyzer dialysate inlet 326 and dialyzer dialysate entry portal 330, as well as dialyzer cleaning fluid exit portal 336 are shown connected to dialyzer first end cap 322. Similarly, dialyzer dialysate outlet 328 and its dialyzer dialysate exit portal 332, as well as dialyzer cleaning fluid entry portal 340 are shown connected to dialyzer second end cap 324. First dialyzer 114 includes a dialyzer interior 342, defined by a dialyzer interior surface 344. Dialyzer exterior surface 310 and dialyzer interior surface 344 define either side of the dialyzer well.

Figure 7B:
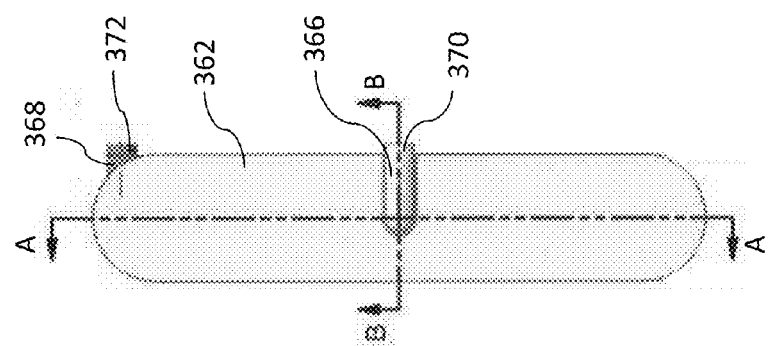
FIG. 7B is a side view of the cleaning column shown in FIG. 7A.
Figure 7A:
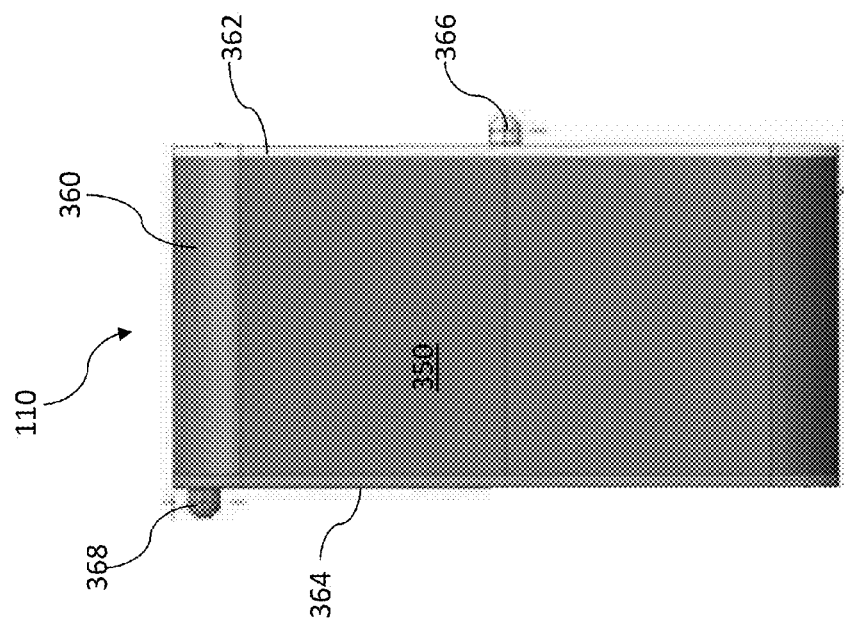
FIG. 7A is a top, plan view of a cleaning column that can be used as part of a wearable artificial kidney in accordance with the present invention.

FIG. 7A is a top, plan view of first cleaning column 110, which also corresponds to second cleaning column 120. First cleaning column 110 includes a cleaning column exterior surface 350. First cleaning column 110 includes a cleaning column main-housing 360 and on opposing ends, a cleaning column entry cap 362 and a cleaning column exit cap 364, respectively. A cleaning column inlet 366 is located on cleaning column entry cap 362 and cleaning column outlet 368 is located on cleaning column exit cap 364.

FIG. 7B is a side view of first cleaning column 110 shown in FIG. 7A. Cleaning column entry cap 362 is visible, including cleaning column inlet 366, having a cleaning column entry portal 370. Cleaning column 368, having a cleaning column exit portal 372, is also visible.

Figure 7D:
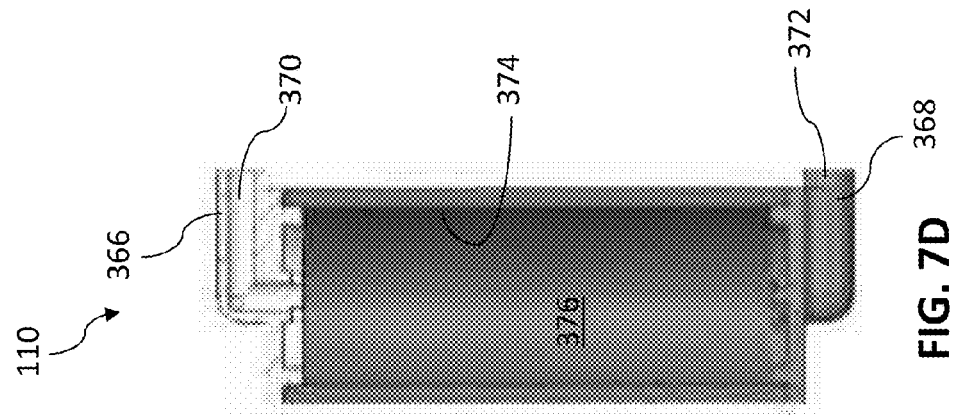
FIG. 7D is another view of the cleaning column shown in FIG. 7A, perpendicular to the cross-sectional view shown in FIG. 7C, and shown in partial cross-section.
Figure 7C:
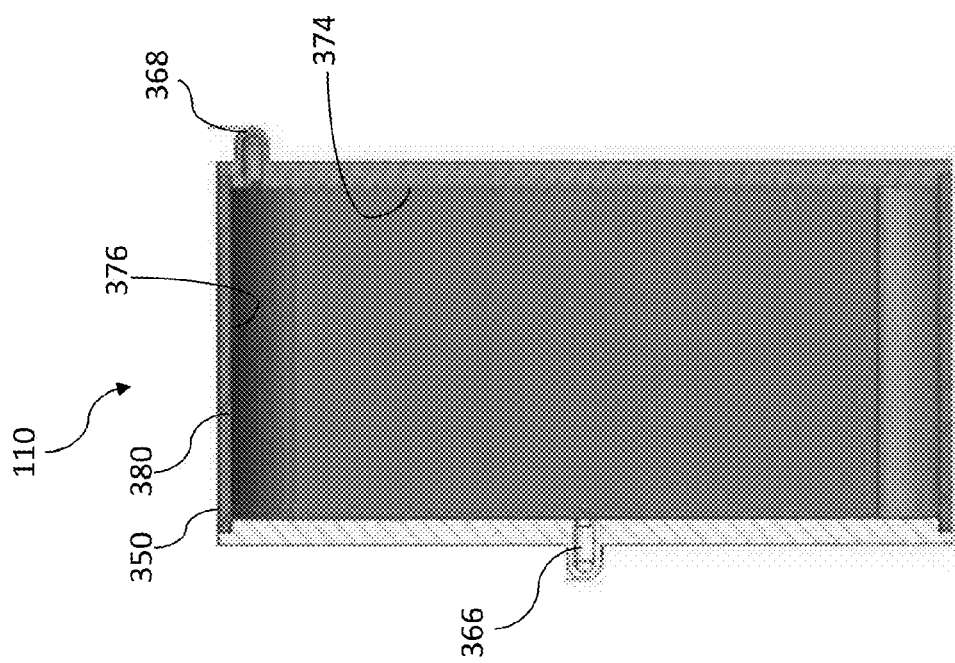
FIG. 7C is a cross-sectional view of the cleaning column shown in FIGS. 7A and 7B, taken alone line A-A of FIG. 7B.

FIG. 7C is a cross-sectional view of first cleaning column 110 shown in FIG. 7A taken along line A-A depicted in FIG. 7B. Cleaning column inlet 366 and column outlet 368 are visible. Cleaning column interior 374 is shown defined by cleaning column interior surface 376. Cleaning column interior surface 376 and cleaning column exterior surface 350 define cleaning column wall 380.

FIG. 7D is a cross-sectional view of first cleaning column 110 shown in FIG. 7A, taken along line B-B shown in FIG. 7B. In FIG. 7D, cleaning column inlet 366 and its cleaning column entry portal 370 are visible as well as cleaning column outlet 368 and its cleaning column exit portal 372. Cleaning column interior 374 is shown defined by cleaning column interior surface 376.

It is apparent that variations and modifications to the present invention are possible without departing from its scope and spirit. It is therefore to be understood that the appended claims are to be construed as encompassing all features of patentable novelty that reside in the present invention, including all features that would be treated as equivalent thereof by those skilled in the art to which the present invention pertains. All U.S., International, and foreign patents and publications, as well as non-patent literature, referred to herein are hereby incorporated herein by reference in their entireties. All publications, patents, and patent applications mentioned in this specification are herein incorporated by reference to the same extent as if each individual publication, patent, or patent application was specifically and individually indicated to be incorporated by reference.

What is claimed is:

1. A flexible manifold configured for use as part of a wearable artificial kidney, the flexible manifold comprising:
   an array of manifold plates comprising
      a first manifold plate comprising a first lateral edge, a first portal, and a first conduit in fluid communication with the first portal,
      a second manifold plate comprising a second lateral edge, a second portal, a second conduit in fluid communication with the second portal, a third lateral edge, a third portal, and a third conduit in fluid communication with the third portal, the first lateral edge positioned adjacent to the second lateral edge, and
      a third manifold plate comprising a fourth lateral edge, a fourth portal along the fourth lateral edge, and a fourth conduit in fluid communication with the fourth portal, the third lateral edge positioned adjacent to the fourth lateral edge;
   a first flexible hinge joining the first manifold plate and the second manifold plate at the first and second lateral edges, the first flexible hinge comprising a first flexible tube joining the first conduit and the second conduit to form a first flow path; and
   a second flexible hinge joining the second manifold plate and the third manifold plate at the third and fourth lateral edges, the second flexible hinge comprising a second flexible tube joining the fourth conduit in fluid communication with the second conduit to form a segment of the first flow path.

2. The flexible manifold of claim 1, wherein:
   the first manifold plate further comprises a fifth portal and a fifth conduit in fluid communication with the fifth portal; and
   the first flexible hinge further comprises a third flexible tube joining the fifth conduit and the third conduit to form a second flow path.

3. The flexible manifold of claim 2, wherein:
   the first manifold plate further comprises a sixth portal and a sixth conduit in fluid communication with the sixth portal;
   the second manifold plate further comprises a seventh portal and a seventh conduit in fluid communication with the seventh portal; and
   the first flexible hinge further comprises a fourth flexible tube joining the sixth conduit and the seventh conduit to form a third flow path.

4. A flexible manifold configured for use as part of a wearable artificial kidney, the flexible manifold comprising:
   an array of manifold plates comprising
      a first manifold plate comprising a first lateral edge, a first portal, a first conduit in fluid communication with the first portal, a third portal, a third conduit in fluid communication with the third portal, a fifth portal, and a fifth conduit in fluid communication with the fifth portal,
      a second manifold plate comprising a second lateral edge, a third lateral edge, a second portal, a second conduit in fluid communication with the second portal, a fourth portal, a fourth conduit in fluid communication with the fourth portal, a sixth portal, a sixth conduit in fluid communication with the sixth portal, the first lateral edge being positioned adjacent to the second lateral edge, and a third manifold plate comprising a fourth lateral edge, a seventh portal along the fourth lateral edge, and a seventh conduit in fluid communication with the seventh portal;

a first flexible hinge joining the first manifold plate and the second manifold plate at the first and second lateral edges, the first flexible hinge comprising a first flexible tube joining the first conduit and the second conduit to form a first flow path, a second flexible tube joining the third conduit and the fourth conduit to form a second flow path, and a third flexible tube joining the fifth conduit and the sixth conduit to form a third flow path; and a second flexible hinge joining the second manifold plate and the third manifold plate at the third and fourth lateral edges, the second flexible hinge comprising a fourth flexible tube joining the seventh conduit in fluid communication with the second conduit, or sixth conduit to form a segment of the first or third flow paths.

5. The flexible manifold of claim 4, wherein:
the first flow path further comprises an eighth conduit in the first manifold plate, a ninth conduit in the second manifold plate, a tenth conduit in the second manifold plate, an eleventh conduit in the second manifold plate, a twelfth conduit in the second manifold plate, a thirteenth conduit in the third manifold plate, and the seventh conduit in the third manifold plate;
the first flexible hinge further comprises a fifth flexible tube joining the eight conduit and the ninth conduit; and
the second flexible hinge further comprises
a sixth flexible tube joining the tenth conduit and the thirteen conduit,
a seventh flexible tube joining the thirteenth conduit and the eleventh conduit, and
an eighth flexible tube joining the seventh conduit and the twelfth conduit.

6. The flexible manifold of claim 5, wherein:
the second flow path further comprises a fourteenth conduit in the first manifold plate, a fifteenth conduit in the first manifold plate, and a sixteenth conduit in the second manifold plate, and a first loop tube joining the third conduit and the fourteenth conduit in fluid communication.

7. The flexible manifold of claim 6, wherein:
the third flow path further comprises a seventeenth conduit in first manifold plate, an eighteen conduit in the second manifold plate, a nineteenth conduit in the second manifold plate, a twentieth conduit in the third manifold plate, a twenty-first conduit in the third manifold plate, and a second loop tube joining the fifth conduit and the seventeenth conduit in fluid communication;
the first flexible hinge further comprises a tenth flexible tube joining the seventeenth conduit and the eighteenth conduit; and
the second flexible hinge further comprises an eleventh flexible tube joining the eighteenth conduit and the twentieth conduit, and a twelfth flexible tube joining the nineteenth conduit and the twenty-first conduit.

8. The flexible manifold of claim 7, wherein:
the first manifold plate further comprises a first cleaning column inlet connector portal in fluid communication with the second flow path and a first cleaning column outlet connector portal in fluid communication with the second flow path;

the second manifold plate further comprises a first dialyzer dialysate inlet connector portal in fluid communication with the first flow path, a first dialyzer dialysate outlet portal in fluid communication with the first flow path, a first dialyzer cleaning fluid inlet connector portal in fluid communication with the second flow path, a first dialyzer cleaning fluid outlet connector portal in fluid communication with the second flow path, a second dialyzer dialysate inlet connector portal in fluid communication with the first flow path, a second dialyzer dialysate outlet portal in fluid communication with the first flow path, a second dialyzer cleaning fluid inlet connector portal in fluid communication with the third flow path, and a second dialyzer cleaning fluid outlet connector portal in fluid communication with the third flow path; and
the third manifold plate further comprises a second cleaning column inlet connector portal in fluid communication with the third flow path and a second cleaning column outlet connector portal in fluid communication with the third flow path.

9. A wearable artificial kidney comprising:
the flexible manifold of claim 8;
a first cleaning column in fluid communication with the second flow path and comprising a first cleaning column inlet connected to the first cleaning column inlet connector portal and a first cleaning column outlet connected to the first cleaning column outlet connector portal;
a first dialyzer in fluid communication with the first and second flow paths and comprising a first dialyzer inlet connected to the first dialyzer dialysate inlet connector portal, a first dialyzer dialysate outlet connected to the first dialyzer dialysate outlet portal, a first dialyzer cleaning fluid inlet connected to the first dialyzer cleaning fluid inlet connector portal, and a first dialyzer cleaning fluid outlet connector connected to the first dialyzer cleaning fluid outlet connector portal;
a second dialyzer in fluid communication with the first and third flow paths and comprising a second dialyzer inlet connected to the second dialyzer dialysate inlet connector portal, a first dialyzer dialysate outlet connected to the first dialyzer dialysate outlet portal, a second dialyzer cleaning fluid inlet connected to the second dialyzer cleaning fluid inlet connector portal, and a second dialyzer cleaning fluid outlet connector connected to the second dialyzer cleaning fluid outlet connector portal; and
a second cleaning column in fluid communication with the third flow path comprising a second cleaning column inlet connected to the second cleaning column inlet connector portal and a second cleaning column outlet connected to the second cleaning column outlet connector portal.

10. The wearable artificial kidney of claim 9, further comprising
a first pump in operable communication with the first flow path;
a second pump in operable communication with the second flow path; and
a third pump in operable communication with the third flow path.

11. The wearable artificial kidney of claim 10, wherein the second and third pumps are peristaltic pumps, the second pump engages the second loop tube, and the third pump engages the third loop tube.

12. The wearable artificial kidney of claim 9, wherein the first dialyzer comprises a membrane selectively-permeable to anions and the first cleaning column comprises a first layer comprising activated carbon and a second layer comprising an anion exchange resin, hydrous zirconium oxide, or a combination thereof.

13. The wearable artificial kidney of claim 9, wherein the second dialyzer comprises a membrane selectively-permeable to urea and the second cleaning column comprises an acid cation exchange resin, an ion exchange sorbent, or a combination thereof.

14. The wearable artificial kidney of claim 9, wherein the second dialyzer comprises a membrane selectively-permeable to urea and the second cleaning column comprises a first layer comprising urease and a second layer comprising an acid cation exchange resin, an ion exchange sorbent, or a combination thereof.

15. The wearable artificial kidney of claim 9, further comprising a strap, belt, harness, frame, holster, or other attachment device configured to attach the flexible manifold to a dialysis patient.

16. A system comprising:
the wearable artificial kidney of claim 9;
a manifold inlet line configured to be in fluid communication with a peritoneal cavity of a dialysis patient and the first flow path;
a manifold outlet line configured to be in fluid communication with the peritoneal cavity of the dialysis patient, and the first flow path;
a dialysate fluid in the first flow path;
a first cleaning fluid in the second flow path; and
a second cleaning fluid in the third flow path.

17. A method of regenerating dialysate fluid in the system of claim 16, the method comprising:
cycling the dialysate fluid in the first flow path;
cycling the first cleaning fluid in the second flow path; and
cycling the second cleaning fluid in the second flow path;
wherein dialysate fluid is in need of regeneration before entering the flexible manifold and has been regenerated once the dialysate fluid has exited the flexible manifold.

18. The method of claim 17, further comprising replacing one or more of the first cleaning column, the first dialyzer, the second dialyzer, and the second cleaning column, and repeating the cycling of the dialysate fluid, the first cleaning fluid, and the second cleaning fluid.

19. A wearable artificial kidney comprising:
a flexible manifold comprising a first manifold plate, a second manifold plate joined to the first manifold plate by a first flexible hinge, and a third manifold plate joined to the second manifold plate by a second flexible hinge;
a first flow path comprising one or more conduits located in one or more of the first, second, and third manifold plates;
a second flow path comprising one or more conduits located in one or more of the first, second, and third manifold plates;
a third flow path comprising one or more conduits located in one or more of the first, second, and third manifold plates;
a first cleaning column mounted on the first manifold plate and in fluid communication with the second flow path;
a first dialyzer mounted on the second manifold plate and in fluid communication with the first and second flow paths;
a second dialyzer mounted on the second manifold plate and in fluid communication with the first and third flow paths;
a second cleaning column mounted on the third manifold plate in fluid communication with the third flow path; and
at least one pump configured to cycle a dialysate fluid through the first flow path, a first cleaning fluid through the second flow path, and a second cleaning fluid through the third flow path.

20. The wearable artificial kidney of the claim 19, wherein:
the first dialyzer comprises a membrane selectively-permeable to anions;
the first cleaning column comprises a first layer comprising activated carbon and a second layer comprising an anion exchange resin, hydrous zirconium oxide, or a combination thereof;
the second dialyzer comprises a membrane selectively-permeable to urea; and
the second cleaning column comprises a first layer comprising urease and a second layer comprising an acid cation exchange resin, an ion exchange sorbent, or a combination thereof.

* * * * *